United States Patent
Goell et al.

(10) Patent No.: US 8,280,212 B2
(45) Date of Patent: Oct. 2, 2012

(54) PHOTONIC CRYSTAL FIBERS HAVING A PREFERRED BENDING PLANE AND SYSTEMS THAT USE SUCH FIBERS

(75) Inventors: James Goell, Lexington, MA (US);
Marin Soljacic, Belmont, MA (US);
Steven A. Jacobs, Needham, MA (US);
Tairan Wang, Waltham, MA (US);
Gokhan Ulu, Roslindale, MA (US);
Burak Temelkuran, Boston, MA (US);
Steven G. Johnson, Cambridge, MA (US)

(73) Assignee: OmniGuide, Inc., Cambridge, MA (US)

( * ) Notice: Subject to any disclaimer, the term of this patent is extended or adjusted under 35 U.S.C. 154(b) by 1475 days.

(21) Appl. No.: 11/366,345

(22) Filed: Mar. 2, 2006

(65) Prior Publication Data
US 2007/0053640 A1    Mar. 8, 2007

Related U.S. Application Data

(63) Continuation-in-part of application No. 11/101,915, filed on Apr. 8, 2005, now Pat. No. 7,167,622.

(60) Provisional application No. 60/658,531, filed on Mar. 4, 2005.

(51) Int. Cl.
*G02B 6/02* (2006.01)
(52) U.S. Cl. ........................ 385/123; 385/125
(58) Field of Classification Search ........... 385/123–128
See application file for complete search history.

(56) References Cited

U.S. PATENT DOCUMENTS

| | | | |
|---|---|---|---|
| 3,467,098 A | 9/1969 | Ayers | |
| 3,659,915 A | 5/1972 | Maurer et al. | |
| 3,858,577 A | 1/1975 | Bass et al. | |
| 4,076,380 A | 2/1978 | MiMarcello et al. | |
| 4,099,835 A | 7/1978 | French et al. | |
| 4,170,997 A | 10/1979 | Pinnow et al. | |
| 4,583,526 A | 4/1986 | Ali | |
| 4,583,539 A * | 4/1986 | Karlin et al. | 606/4 |
| 4,652,083 A | 3/1987 | Laakmann | |
| 4,672,969 A | 6/1987 | Dew | |
| 4,688,892 A | 8/1987 | Laakmann | |
| 4,688,893 A | 8/1987 | Laakmann | |
| 4,805,987 A | 2/1989 | Laakmann et al. | |
| 4,806,289 A | 2/1989 | Laursen et al. | |
| 4,911,712 A | 3/1990 | Harrington | |
| 4,913,505 A | 4/1990 | Levy | |
| 4,917,084 A | 4/1990 | Sinofsky | |

(Continued)

FOREIGN PATENT DOCUMENTS
EP    0 844 501    5/1998

(Continued)

OTHER PUBLICATIONS

International Search Report for PCT/US2006/007437 by Mildred Condon and W. Elflein dated Jul. 13, 2006.

(Continued)

*Primary Examiner* — Kevin S Wood
(74) *Attorney, Agent, or Firm* — Goodwin Procter LLP

(57) ABSTRACT

In general, in a first aspect, the invention features photonic crystal fibers that include a core extending along a waveguide axis, a confinement region extending along the waveguide axis surrounding the core, and a cladding extending along the waveguide axis surrounding the confinement region, wherein the cladding has an asymmetric cross-section.

25 Claims, 12 Drawing Sheets

U.S. PATENT DOCUMENTS

| | | | |
|---|---|---|---|
| 4,930,863 A | 6/1990 | Croitoriu et al. | |
| 4,932,749 A | 6/1990 | Haidle et al. | |
| 4,947,540 A | 8/1990 | Komachi | |
| 5,002,051 A | 3/1991 | Dew et al. | |
| 5,005,944 A | 4/1991 | Laakmann et al. | |
| 5,030,217 A | 7/1991 | Harrington | |
| 5,071,222 A | 12/1991 | Laakmann et al. | |
| 5,139,494 A | 8/1992 | Freiberg | |
| 5,140,984 A | 8/1992 | Dew et al. | |
| 5,276,761 A | 1/1994 | Shimoyama et al. | |
| 5,288,288 A | 2/1994 | Lewis et al. | |
| 5,325,458 A | 6/1994 | Morrow et al. | |
| 5,423,805 A | 6/1995 | Brucker et al. | |
| 5,440,664 A | 8/1995 | Harrington et al. | |
| 5,480,050 A | 1/1996 | Morrow et al. | |
| 5,497,440 A | 3/1996 | Croitoriu et al. | |
| 5,497,441 A | 3/1996 | Croitoru et al. | |
| 5,558,668 A | 9/1996 | Lankford et al. | |
| 5,567,471 A | 10/1996 | Harrington et al. | |
| 5,630,807 A | 5/1997 | Joffe | |
| 5,729,646 A | 3/1998 | Miyagi et al. | |
| 5,815,627 A | 9/1998 | Harrington | |
| 5,830,209 A | 11/1998 | Savage et al. | |
| 5,843,073 A | 12/1998 | Sinofsky | |
| 5,935,491 A | 8/1999 | Tripathy et al. | |
| 5,951,543 A | 9/1999 | Brauer | |
| 5,995,696 A | 11/1999 | Miyagi et al. | |
| 6,104,853 A | 8/2000 | Miyagi et al. | |
| 6,130,780 A | 10/2000 | Joannopoulos et al. | |
| 6,141,476 A | 10/2000 | Matsuura et al. | |
| 6,165,205 A | 12/2000 | Neuberger | |
| 6,172,810 B1 | 1/2001 | Fleming et al. | |
| 6,343,174 B1 | 1/2002 | Neuberger | |
| 6,404,966 B1 | 6/2002 | Kawanishi et al. | |
| 6,463,200 B2 | 10/2002 | Fink et al. | |
| 6,527,764 B1 | 3/2003 | Neuberger et al. | |
| 6,547,780 B1 | 4/2003 | Sinofsky | |
| 6,563,981 B2 | 5/2003 | Weisberg et al. | |
| 6,603,911 B2 | 8/2003 | Fink et al. | |
| 6,606,440 B2 | 8/2003 | Hasegawa et al. | |
| 6,625,364 B2 | 9/2003 | Johnson et al. | |
| 6,683,277 B1 | 1/2004 | Millard et al. | |
| 6,728,439 B2 | 4/2004 | Weisberg et al. | |
| 6,735,369 B2 | 5/2004 | Komachi et al. | |
| 6,788,864 B2 | 9/2004 | Ahmad et al. | |
| 6,801,698 B2 | 10/2004 | King et al. | |
| 6,816,243 B2 | 11/2004 | Shurgalin et al. | |
| 6,879,386 B2 | 4/2005 | Shurgalin et al. | |
| 6,895,154 B2 | 5/2005 | Johnson et al. | |
| 6,898,359 B2 | 5/2005 | Soljacic et al. | |
| 6,903,873 B1 | 6/2005 | Joannopoulos et al. | |
| 6,986,739 B2 | 1/2006 | Warren et al. | |
| 7,180,598 B2 * | 2/2007 | Willig et al. | 356/460 |
| 2002/0150364 A1 | 10/2002 | Bassett et al. | |
| 2002/0164137 A1 | 11/2002 | Johnson et al. | |
| 2003/0031852 A1 | 2/2003 | Fink et al. | |
| 2003/0044158 A1 | 3/2003 | King et al. | |
| 2003/0044159 A1 | 3/2003 | Anderson et al. | |
| 2003/0100824 A1 | 5/2003 | Warren et al. | |
| 2004/0013379 A1 | 1/2004 | Johnson et al. | |
| 2004/0137168 A1 | 7/2004 | Fuflyigin | |
| 2004/0141702 A1 | 7/2004 | Fuflyigin et al. | |
| 2004/0223715 A1 * | 11/2004 | Benoit et al. | 385/123 |
| 2005/0226579 A1 | 10/2005 | Fink et al. | |
| 2005/0259933 A1 | 11/2005 | Temelkuran et al. | |
| 2005/0259934 A1 | 11/2005 | Temelkuran et al. | |
| 2005/0259942 A1 | 11/2005 | Temelkuran et al. | |
| 2005/0259944 A1 | 11/2005 | Anderson et al. | |
| 2005/0271340 A1 | 12/2005 | Weisberg et al. | |

FOREIGN PATENT DOCUMENTS

| | | |
|---|---|---|
| GB | 1198904 | 5/1968 |
| JP | 2003222740 | 8/2003 |
| WO | WO 99/47465 | 9/1999 |
| WO | WO 00/22466 | 4/2000 |
| WO | WO 00/43815 | 7/2000 |
| WO | WO 00/46287 | 8/2000 |
| WO | WO 02/41050 | 5/2002 |
| WO | WO 02/061467 | 8/2002 |
| WO | WO 02/072489 | 9/2002 |
| WO | WO 03/050571 | 6/2003 |
| WO | WO 03/079073 | 9/2003 |
| WO | WO 03/079077 | 9/2003 |
| WO | WO 2004/058328 A2 | 7/2004 |
| WO | WO2004/064623 A2 | 8/2004 |

OTHER PUBLICATIONS

Search report, Oct. 27, 2005, PCT/US05/12047.

European Search Report for Application No. / Patent No.—03796927.6 / PCT/US0339344, dated May 12, 2006.

Allan et al. "Photonic crystal fibers: effective-index and band-gap guidance." Photonic Crystals and Light Localization in the $21^{st}$ Century. 2001: Kluwer. pp. 305-320.

Barkou et al. "Silica-air photonic crystal fiber design that permits waveguiding by a true photonic bandgap effect." Optics Letters, 24:1, Jan. 1, 1999, pp. 46-48.

Baumeister, P. "the transmission and degree of polarization of quarter-wave stacks at non-normal incidence." Opt. Acta, 8, 1961, pp. 105-119.

Birks et al. "Full 2-D photonic bandgaps in silica/air structures." Electronic Letters, 31:22, Oct. 26, 1995, pp. 1941-1943.

Bormashenko et al. "Development of new-near-infrared filters based on the 'sandwich' polymer-chalcogenide glass-polymer composites." Optical Engineering, 40:5, 2001, pp. 661-662.

Bormashenko et al. "New Oriented Polymer/Thermoplastic Glass Composites for IR Optics." Engineering Materials, 10, 2000, pp. 657-658.

Bormashenko et al. "Optical Properties and infrared optics applications of composite films based on polyethylene and low-melting-point chalcogendie." Society of Photo-Optical Instrumentation Engineers, Feb. 2002. pp. 295-302.

Bornstein et al. "Chalcogenide Hollow Fibers." Journal of Non-Crystalline Solids, 77:8, 1985, pp. 1277-1280.

Broeng et al. "Analysis of air-guiding photonic bandgap fibers." Optics Letters, 25:2, 2000, pp. 96-98.

Cregan et al. "Single-Mode Photonic Band Gap Guidance of Light in Air." Science, 285, Sep. 3, 1999, pp. 1537-1539.

Dai et al. "High-peak-power, pulsed $CO_2$ laser light delivery by hollow glass waveguides." Appl Optics, 36, 1997, pp. 5072-5077.

De Sterke et al. "Differential losses in Bragg fibers." J. Appl. Phys., 76:2, Jul. 15, 1994, pp. 680-688.

Eggleton et al. Microstructured optical fiber devices. Optics Express, 9:13, 2001, pp. 698-713.

Feigel A. et al. "Chalcogenide glass-based three-dimensional photonic crystals." Applied Physics Letters, 77:20, pp. 3221-3223, Nov. 13, 2000.

Fink et al. "A dielectric omnidirectional reflector." Science, 282:5394, 1998, pp. 1679-1682.

Fink et al. "Guiding Optical Light in Air Using an All-Dielectric Structure." Journal of Lightwave Technology, 17:11, Nov. 11, 1999, pp. 2039-2041.

Fitt et al. "Modeling the fabrication of hollow fibers: Capillary drawings." Journal of Lightwave Technology, 19:12, 2001, pp. 1924-1931.

Gopal et al. "Deposition and characterization of metal sulfide dielectric coatings for hollow glass waveguide." Optical Society of America, 2003. Optics Express, 11:24, Dec. 1, 2003.

Harrington, J.A. "Infrared Fibers in Handbook of Optics." McGraw-Hill, 2001, pp. 14, 1-14, 13.

Harrington, James. "A Review of IR Transmitting, Hollow Waveguides." Fiber and Integrated Optics, 19, 2000, pp. 211-217.

Hart et al. "External Reflection from Omnidirectional Dielectric Mirror Fibers." Science, 296, Apr. 19, 2002, pp. 510-513.

Hilton, A.R., "Optical Properties of Chalcogenide Glasses." Journal of Non-Crystalline Solids, 2, 1970, pp. 28-39.

Akihito Hongo et al., "Infrared Hollow Fibers for Medical Applications", Hitachi Cable Review No. 23, Aug. 2004.

Hongo et al. "Transmission of Kilowatt-Class Co2-Laser Light through Dielectric-Coated Metallic Hollow Wave-Guides for Material Processing." Applied Optics, 31:24, 1992. pp. 5114-5120.

Ibanescu et al. "An all-dielectric coaxial waveguide." Science, 289:5478, 2000, pp. 415-419.

Ibanescu et al. "Analysis of Mode Structure in OmniGuide Fibers." Physical Review E, 67:4, 2003.

Ivanenko et al. "In vitro incision of bone tissue with a Q-switch $CO_2$ laser. Histological examination." Lasers in the Life Sciences, vol. 9, pp. 171-179 (2000).

John F. Ready "4.8 Process Gas Nozzles—Chapter 4: Components for Laser Materials Processing Systems" LIA Handbook of Laser Materials Processing, pp. 155-159 (2001).

John, S. "Strong Localization of Photons in Certain Disordered Dielectric Superlattices." Physical Review Letters, 58:23, 1987, pp. 2486-2489.

Johnson et al. "Low-loss asymptotically single-mode propagation in large-core OmniGuide fibers." Optics Express, 9:13, 2001, pp. 748-779.

Keck et al. "On the ultimate lower limit of attenuation in glass optical waveguides." Applied Physics Letters, 22:7, 1973, pp. 307-309.

King et al "Laboratory preparation of highly pure $As_2Se_3$ glass." J. Non-Cryst. Sol., 181, 1995, pp. 231-237.

Knight et al. "Photonic Band Gap Guidance in Optical Fibers." Science, 282, Nov. 20, 1998, pp. 1476-1478.

Kucuk et al. "An estimation of the surface tension for silicate glass melts at 1400° C. using statistical analysis." Glass Technol., 40, 1999, pp. 149-153.

Mahlein. Generalized Brewster-angle conditions for quarter-wave multilayers at non-normal incidence. J. Opt. Soc. Am., 64, 1974, pp. 647-653.

Marcatilli et al. "Hollow metallic and dielectric waveguides for long distance optical transmission and lasers." Bell Syst. Tech. J., 43, 1964, pp. 1783-1809.

Mossadegh R. et al. "Fabrication of single-mode chalcogenide optial fiber." Journal of Lightwave Technology, 16:2, pp. 214-216, Feb. 1998.

Matsuura et al. "Hollow infrared fibers fabricated by glass-drawing technique." Optics Express, 10:12, 2002, pp. 488-492.

Matsuura et al. "Small-bore hollow waveguide for delivery of near singlemode IR laster radiation." Electronic Letters, 30, 1994, pp. 1688-1690.

Mitra et al. "Nonlinear limits to the information capacity of optical fibre communications." Nature, 411, 2001, pp. 1027-1030.

Miyagi et al. "Design Theory of Dielectric-Coated Circular Metallic Waveguides for Infrared Transmission." Journal of Lightwave Technology, 2:2, 1984, pp. 116-126.

Monro, T.M. et al. "Chalcogenide Holey Fibres." Electronics Letters, 36:24, pp. 1998-2000, Nov. 23, 2000.

Nishii, J. et al. "Chalcogenide glass fiber with a core-cladding structure." Applied Optics, 28: 23, pp. 5122-5127, Dec. 1, 1989.

Nubling et al. "Hollow-waveguide delivery systems for high-power, industrial $CO_2$ lasers." Applied Optics, 34:3, Jan. 20, 1996, pp. 372-380.

Ouyang et al. "Comparative study of air-core and coaxial Bragg fibers: single-mode transmission and dispersion characteristics." Optics Express, 9:13, 2001, pp. 733-747.

Pottage et al. "Robust photonic band gaps for hollow core guidance in PCF made from high index glass." Optics Express, 11:22, Nov. 3, 2003, pp. 2854-2861.

Renn et al. "Laser-Guided Atoms in Hollow-Core Optical Fibers." Physical Review Letters, 75:18, 1995, pp. 3253-3256.

Rundquist et al. "Phase-matched generation of coherent soft-X-rays." Science, 280:5368, 1998, pp. 1412-1415.

Sanghera et al. "Development and Infrared Applications of Chalcogenide Glass Optical Fibers." Fiber and Integrated Optics, 19:251, 2000, pp. 251-274.

Sanghera et al. "Active and passive chalcogenide glass optical fibers for IR applications: a review." Journal of Non-Crystalline Solids, 257, 1999, pp. 6-16.

Sanghera, J.S. et al. "Fabrication of long lengths of low-loss IR transmitting AS40S (60-X) sex glass fibers." Journal of Lightwave Technology, 14:5, pp. 743-748, May 1, 1996.

Seddon, A.B. "Chalcogenide glasses: a review of their preparation, properties and applications." J. Non-Cyrst. Sol., 184, 1995, pp. 44-50.

Temelkuran et al. "Wavelength-scalable hollow optical fibres with large photonic bandgaps for $CO_2$ laser transmission." Nature, 420, Dec. 12, 2002, pp. 650-653.

Temelkuran et al. "Low-loss infrared dielectric materials system for broadband dual-rang omnidirectional reflectivity." Optics Letters, 26, 2001, pp. 1370-1372.

Tones et al. "OmniGuide Photonic Bandgap Fibers for flexible Delivery of $CO_2$ Lasers in Laryngology" Proceedings of SPIE, vol. 5686, pp. 310-321 (Apr. 2005).

Varsheneya A.K. Fundamentals of Inorganic Glasses, Academic Press, San Diego, pp. 5-7,1994.

Varshneya, A. K. "Some comments on physical properties of chalcogenide glasses." J. Non-Cryst. Sol., 273, 2000, pp. 1-7.

Vienne et al. "First demonstration of air-silica Bragg fiber." Optical Society of America, 2003. Institute of Electrical and Electronics Engineers. Optical Fiber Communication Conference and Exposition Postdeadline Papers.

Weber et al. Giant Birefringent Optics in Multilayer Polymer Mirrors. Science, 287, 2000, pp. 2451-2456.

Winn et al. Omnidirectional reflection from a one-dimensional photonic crystal. Optics Letters, 23, 1998, pp. 1573-1575.

Yablonovitch. E. "Inhibited Spontaneous Emission in Solid-State Physics and Electronics." Physical Review Letters, 58:20, 1987, pp. 2059-2062.

Yeh et al. "Theory of Bragg Fiber." Journal of the Optical Society of America, 68:9, 1978, pp. 1196-1201.

Yeh et al. Electromagnetic propagation in periodic stratified media. I. General theory. J. Opt. Soc. Am., 67, 1977, pp. 423-438.

"Hollow Fibers for Infrared Laser Light Transmission", Hitachi Cable Review No. 23, Aug. 2004.

* cited by examiner

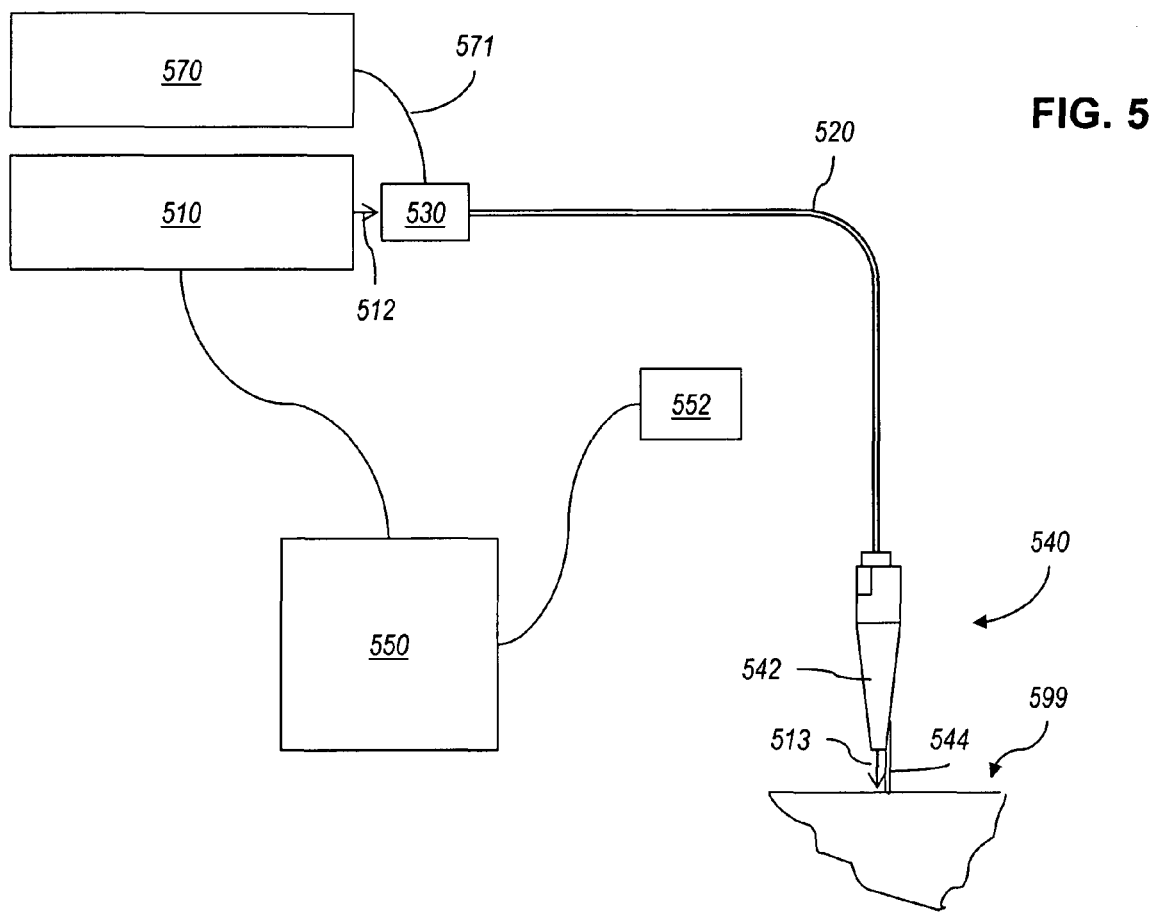

1

PHOTONIC CRYSTAL FIBERS HAVING A PREFERRED BENDING PLANE AND SYSTEMS THAT USE SUCH FIBERS

CROSS-REFERENCE TO RELATED APPLICATIONS

This application is a continuation-in-part application of and claims priority under 35 U.S.C. §120 to U.S. application Ser. No. 11/101,915, entitled "PHOTONIC CRYSTAL FIBERS AND MEDICAL SYSTEMS INCLUDING PHOTONIC CRYSTAL FIBERS," filed on Apr. 8, 2005 now U.S. Pat. No. 7,167,622. This application also claims priority under 35 U.S.C. §119(e)(1) to Provisional Patent Application No. 60/658,531, entitled "PHOTONIC CRYSTAL FIBERS," filed on Mar. 4, 2005. The entire contents of both of the above-mentioned applications are incorporated herein by reference.

BACKGROUND

This invention relates to the field of photonic crystal waveguides and systems using photonic crystal waveguides.

Waveguides play important roles in numerous industries. For example, optical waveguides are widely used in telecommunications networks, where fiber waveguides such as optical fibers are used to carry information between different locations as optical signals. Such waveguides substantially confine the optical signals to propagation along a preferred path or paths. Other applications of optical waveguides include imaging applications, such as in an endoscope, and in optical detection. Optical waveguides can also be used to guide laser radiation (e.g., high intensity laser radiation) from a source to a target in medical (e.g., eye surgery) and manufacturing (e.g., laser machining and forming) applications.

The most prevalent type of fiber waveguide is an optical fiber, which utilizes index guiding to confine an optical signal to a preferred path. Such fibers include a core region extending along a waveguide axis and a cladding region surrounding the core about the waveguide axis and having a refractive index less than that of the core region. Because of the index-contrast, optical rays propagating substantially along the waveguide axis in the higher-index core can undergo total internal reflection (TIR) from the core-cladding interface. As a result, the optical fiber guides one or more modes of electromagnetic (EM) radiation to propagate in the core along the waveguide axis. The number of such guided modes increases with core diameter. Notably, the index-guiding mechanism precludes the presence of any cladding modes lying below the lowest-frequency guided mode for a given wavevector parallel to the waveguide axis. Almost all index-guided optical fibers in use commercially are silica-based in which one or both of the core and cladding are doped with impurities to produce the index contrast and generate the core-cladding interface. For example, commonly used silica optical fibers have indices of about 1.45 and index contrasts ranging from about 0.2% to 3% for wavelengths in the range of 1.5 mm, depending on the application.

Another type of waveguide fiber, one that is not based on TIR index-guiding, is a Bragg fiber, which includes multiple alternating dielectric layers surrounding a core about a waveguide axis. The multiple layers form a cylindrical mirror that confines light to the core over a range of frequencies. The alternating layers are analogous to the alternating layers of a planar dielectric stack reflector (which is also known as a Bragg mirror). The multiple layers form what is known as a photonic crystal, and the Bragg fiber is an example of a photonic crystal fiber. Photonic crystal structures are described generally in Photonic Crystals by John D. Joannopoulos et al. (Princeton University Press, Princeton N.J., 1995).

Drawing a fiber from a preform is the most commonly used method for making fiber waveguides. A preform is a short rod (e.g., 10 to 20 inches long) having the precise form and composition of the desired fiber. The diameter of the preform, however, is much larger than the fiber diameter (e.g., 100's to 1000's of times larger). Typically, when drawing an optical fiber, the material composition of a preform includes a single glass having varying levels of one or more dopants provided in the preform core to increase the core's refractive index relative to the cladding refractive index. This ensures that the material forming the core and cladding are rheologically and chemically similar to be drawn, while still providing sufficient index contrast to support guided modes in the core. To form the fiber from the preform a furnace heats the preform to a temperature at which the glass viscosity is sufficiently low (e.g., less than $10^8$ Poise) to draw fiber from the preform. Upon drawing, the preform necks down to a fiber that has the same cross-sectional composition and structure as the preform. The diameter of the fiber is determined by the specific rheological properties of the fiber and the rate at which it is drawn.

Preforms can be made using many techniques known to those skilled in the art, including modified chemical vapor deposition (MCVD), outside vapor deposition (OVD), plasma activated chemical vapor deposition (PCVD) and vapor axial deposition (VAD). Each process typically involves depositing layers of vaporized raw materials onto a wall of a pre-made tube or rod in the form of soot. Each soot layer is fused shortly after deposition. This results in a preform tube that is subsequently collapsed into a solid rod, over jacketed, and then drawn into fiber.

Optical fibers applications can be limited by wavelength and signal power. Preferably, fibers should be formed from materials that have low absorption of energy at guided wavelengths and should have minimal defects. Where absorption is high, it can reduce signal strength to levels indistinguishable from noise for transmission over long fibers. Even for relatively low absorption materials, absorption by the core and/or cladding heats the fiber. Defects can scatter guided radiation out of the core, which can also lead to heating of the fiber. Above a certain power density, this heating can irreparably damage the fiber. Accordingly, many applications that utilize high power radiation sources use apparatus other than optical fibers to guide the radiation from the source to its destination.

SUMMARY

In general, in a first aspect, the invention features a photonic crystal fiber that includes a core extending along a waveguide axis, a confinement region extending along the waveguide axis, the confinement region surrounding the core, and a cladding extending along the waveguide axis, where the cladding surrounds the confinement region. The cladding has an asymmetric cross-section that extends along a length of the photonic crystal fiber.

Embodiments of the photonic crystal fiber can include one or more of the following features. For example, the confinement region can include a layer of a first material arranged in a spiral structure that extends along the waveguide axis and the asymmetric cross-section causes the photonic crystal fiber to bend preferably in a plane that does not intersect an end of the spiral structure that is adjacent the core. The photonic crystal fiber can be configured to guide radiation at a wavelength λ along the waveguide axis where the confinement region includes a periodic structure that substantially confines the radiation to the core. The cladding can include a layer of a first material surrounding the confinement region, the layer having a thickness along a direction normal to the waveguide axis that is larger than the period of the periodic structure of the confinement region (e.g., the layer thickness can be about 10 times larger than the period, about 20 times larger, about 50 times larger, about 100 times larger, about 200 times larger, about 400 times larger).

In certain embodiments, the asymmetric cross-section causes the photonic crystal fiber to bend preferably in a bend plane relative to other planes.

The confinement region can include a seam extending along the waveguide axis. In some embodiments, the confinement region includes a layer of a first material that is arranged in a spiral around the waveguide axis and the seam is the end of the layer that is adjacent the core. The cladding can have a short cross-sectional dimension, a, non-coincident with the seam. The seam can be located in a range from about 80 degrees to about 110 degrees from the short cross-sectional dimension. The cladding can have a short cross-sectional dimension, a, and a long cross-sectional dimension, b, and an ellipticity, ϵ, given by the formula:

$$\varepsilon = \frac{(b-a)}{\frac{1}{2}(b+a)},$$

that is in a range from about 0.05 to about 0.5 (e.g., about 0.08 or more, about 0.1 or more, about 0.12 or more, about 0.15 or more, about 0.2 or more, about 0.4 or less, about 0.3 or less, such as about 0.25).

The confinement region can include a layer of a first dielectric material arranged in a spiral around the waveguide axis. The confinement region can further include a layer of a second dielectric material arranged in a spiral around the waveguide axis, the second dielectric material having a different refractive index from the first dielectric material. The first dielectric material can be an inorganic dielectric material, such as a glass (e.g., a chalcogenide glass). The second dielectric material can be an inorganic dielectric material, such as a polymer.

In some embodiments, the confinement region includes at least one layer of a chalcogenide glass. In certain embodiments, the dielectric confinement region includes at least one layer of a polymeric material. The core can be a hollow core.

In some embodiments, the photonic crystal fiber is configured to guide radiation at about 10.6 µm along the waveguide axis.

In another aspect, the invention features a system that includes a $CO_2$ laser and the foregoing photonic crystal fiber. The photonic crystal fiber has an input end that is positioned relative to the $CO_2$ laser to receive radiation from the $CO_2$ laser and the photonic crystal fiber being arranged to deliver the radiation to a target.

In a further aspect, the invention features a system that includes the foregoing photonic crystal fiber which has an input end and an output end, and a handpiece attached to the photonic crystal fiber. The handpiece allows an operator to control the orientation of the output end to direct the radiation to a target location of a patient. In some embodiments, the handpiece includes an endoscope. The endoscope can include a flexible conduit and a portion of the photonic crystal fiber is threaded through a channel in the flexible conduit. The endoscope can include an actuator mechanically coupled to the flexible conduit configured to bend a portion of the flexible conduit in at least one plane thereby allowing the operator to vary the orientation of the output end. The photonic crystal fiber can be attached to the endoscope so that the at least one plane corresponds to the bend plane of the photonic crystal fiber.

In general, in another aspect, the invention features a photonic crystal fiber that includes a core extending along a waveguide axis, a confinement region extending along the waveguide axis, the confinement region surrounding the core, and a cladding extending along the waveguide axis, the cladding surrounding the confinement region. The photonic crystal fiber bends preferably in a bend plane relative to other planes.

Embodiments of the photonic crystal fiber can include one or more of the following features and/or one or more features of other aspects.

For example, in some embodiments, the cladding includes a first portion extending along the waveguide axis and a second portion extending along the waveguide axis, the first portion being composed of a first material and the second portion being composed of a second material having a greater stiffness than the first material. The cladding can further include a third portion being composed of a third material having a greater stiffness than the first material. In cross-section, the core can be positioned between the second portion and the third portion. The first portion can surround the second portion.

In general, in a further aspect, the invention features a fiber waveguide that includes a core extending along a waveguide axis, a first portion extending along the waveguide axis, the first portion surrounding the core, and a cladding extending along the waveguide axis, the cladding surrounding the first portion region. An interface between the core and the first portion includes a defect (e.g., a seam) that extends along the waveguide axis and the fiber waveguide bends preferably in a bend plane relative to other planes. Embodiments of the photonic crystal fiber can include one or more features of other aspects.

In general, in a further aspect, the invention features a fiber waveguide that includes a core extending along a waveguide axis, a first portion extending along the waveguide axis, the first portion surrounding the core, and a cladding extending along the waveguide axis, the cladding surrounding the first portion, wherein an interface between the core and the first portion includes a defect (e.g., a seam) that extends along the waveguide axis and the cladding has an asymmetric cross-section that extends along a length of the photonic crystal fiber. Embodiments of the photonic crystal fiber can include one or more features of other aspects.

In general, in a further aspect, the invention features a fiber waveguide that includes a core extending along a waveguide axis, and a first portion extending along the waveguide axis, the first portion surrounding the core, wherein the first portion has an asymmetric cross-section that extends along a length of the photonic crystal fiber. Embodiments of the photonic crystal fiber can include one or more features of other aspects.

In general, in another aspect, the invention features photonic crystal fibers that include a core extending along a waveguide axis, a confinement region extending along the waveguide axis surrounding the core, and a cladding extending along the waveguide axis surrounding the confinement region, wherein the cladding has an asymmetric cross-section.

In general, in another aspect, the invention features photonic crystal fibers that include a core extending along a waveguide axis, a confinement region extending along the waveguide axis surrounding the core, and a cladding extending along the waveguide axis surrounding the confinement region, wherein the photonic crystal fiber bends preferably in a first plane compared to other planes.

In general, in a further aspect, the invention features photonic crystal fibers that include a core extending along a waveguide axis, a confinement region extending along the waveguide axis surrounding the core, and a cladding extending along the waveguide axis surrounding the confinement region, the cladding having a first diameter of a first size and a second diameter of a second size different from the first size.

In general, in another aspect, the invention features photonic crystal fibers that include a core extending along a waveguide axis, a confinement region extending along the waveguide axis surrounding the core, and a cladding extending along the waveguide axis surrounding the confinement region, the cladding having a surface with a cross-section having portions with differing radii of curvature.

Embodiments of the photonic crystal fibers can include one or more of the following features. The confinement region can include a seam. The seam can be non-coincident with the first plane. The seam can be adjacent the core. The cladding can have a short cross-sectional dimension non-coincident with the seam. The seam can be located about 80 degrees or more from the cross-sectional dimension. The seam can be located about 85 degrees or more from the cross-sectional dimension. The seam can be located about 90 degrees from the cross-sectional dimension. The confinement region can have a spiral cross-section. The confinement region can include a chalcogenide glass.

Among other advantages, the photonic crystal fibers can control which portion of a fiber is on the inside or outside of a bend in the fiber. For example, fibers can be designed so that the fiber preferably bends in a way that a seam (or other defect) in the fiber is not positioned on the outside of the bend. Positioning a defect away from the outside of a bend can reduce loss of guided radiation due to the bend, and can reduce fiber failure due to, e.g., heating of the fiber at the defect when the defect is positioned on the outside of a bend.

Accordingly, fibers can be provided that have improved loss characteristics compared with fibers that don't have a preferred bend plane. Improved loss characteristics can result in higher working powers, greater efficiency, and/or longer working lifetimes. Improved loss characteristics can also allow fibers to be used in applications not previously appropriate for the fibers, such as certain high power applications (e.g., high power medical applications).

The details of one or more embodiments of the invention are set forth in the accompanying drawings and the description below. Other features and advantages of the invention will be apparent from the description and drawings, and from the claims.

DESCRIPTION OF DRAWINGS

FIG. 5 is a schematic diagram of a medical laser system that includes a photonic crystal fiber.

Like reference symbols in the various drawings indicate like elements.

DETAILED DESCRIPTION

Figure 1A:
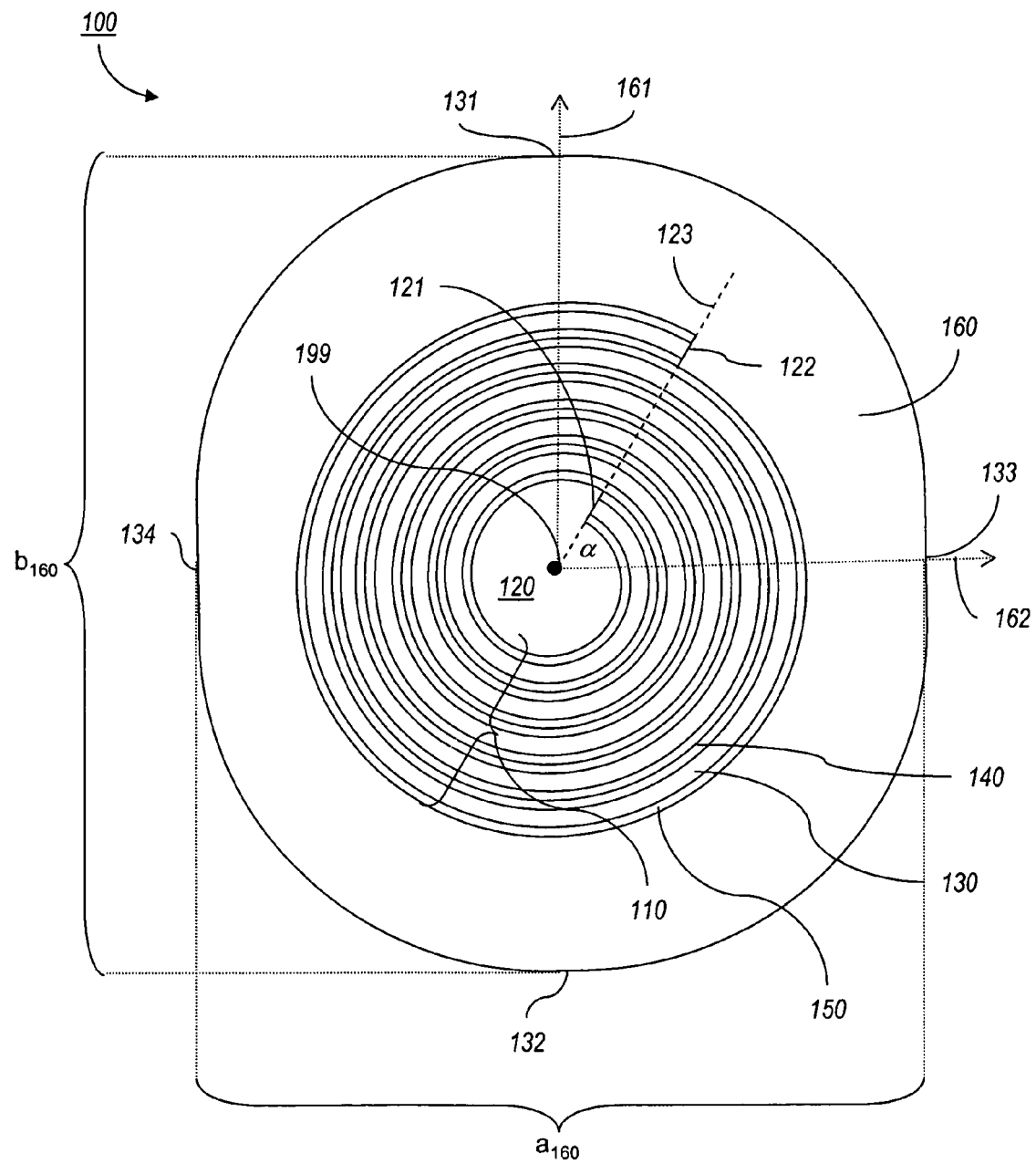
FIG. 1A is a cross-sectional view of an embodiment of a photonic crystal fiber.
Figure 1B:
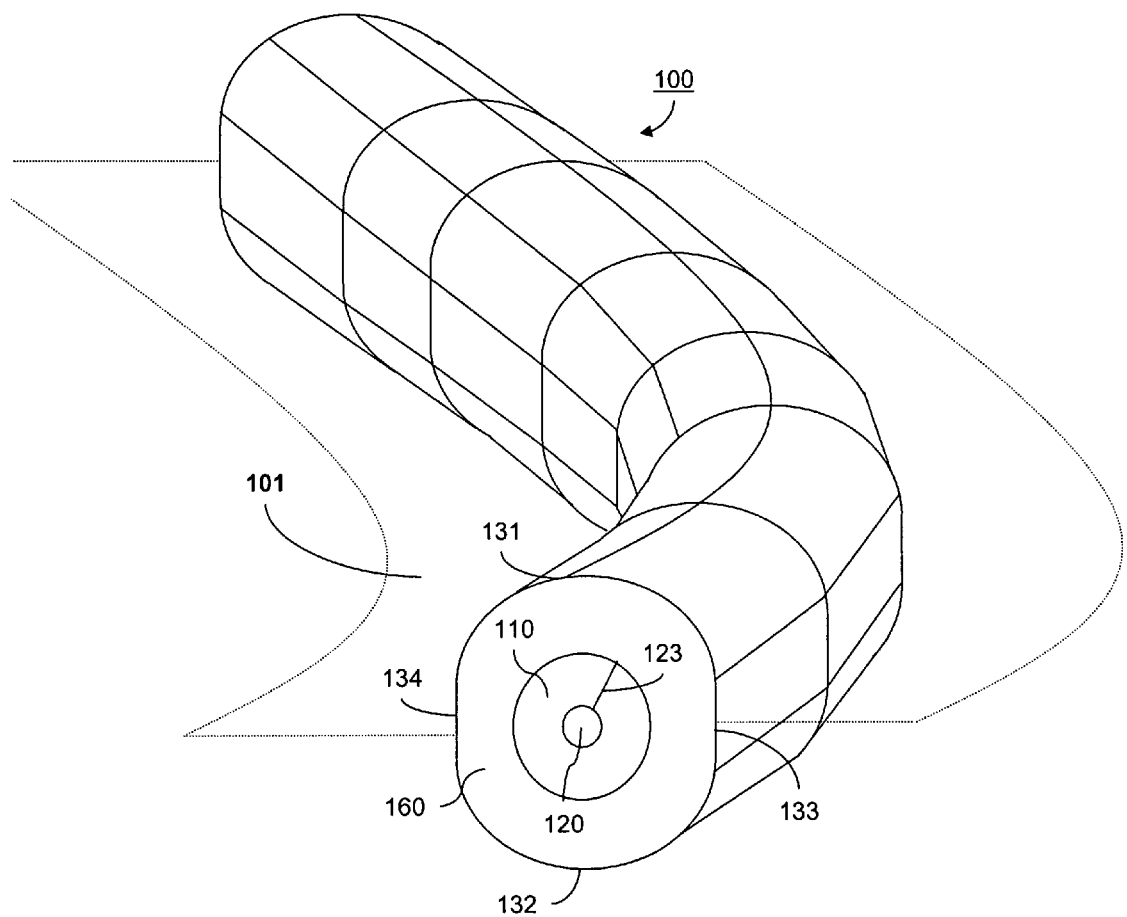
FIG. 1B is a perspective view of the embodiment of the photonic crystal fiber shown in FIG. 1A.

Referring to FIGS. 1A and 1B, a photonic crystal fiber 100 includes a core 120 extending along an axis 199, and a confinement region 110 surrounding the core. A cladding 160 surrounds the confinement region. Photonic crystal fiber 100 is configured to guide radiation at a guiding wavelength $\lambda$ along axis 199. As discussed below, confinement region 110 substantially confines guided radiation at 1 to core 120. Cladding 160 serves primarily to protect and mechanically support confinement region 110.

Cladding 160 has an asymmetric cross-section with a larger diameter along a major axis 161 compared to its diameter along a minor axis 162 orthogonal to the major axis. The major and minor axes are orthogonal to axis 199. The asymmetric cross-section is also manifested in the shape of the cladding's outer surface. In particular, the outer surface of cladding 160 includes portions of differing curvature. In particular, cladding 160 includes arcuate portions 131 and 132 and two straight portions 133 and 134. Arcuate portions 131 and 132 are on opposite sides of the cladding along major axis 121. Straight portions 133 and 134 are on opposite sides of the cladding along minor axis 122. Cladding 160 is co-drawn with confinement region 110 when the fiber is produced.

In general, the asymmetry of the cross-sectional profile of cladding 160 is sufficient to cause fiber 100 to preferably bend in a plane 101 defined by fiber axis 199 and the minor axis 162 during normal use of the fiber. In general, where a fiber has a plane in which the resistance to bending is less than other planes, the plane is referred to as a "bend plane."

The ratio of cladding 160's outer diameter, $b_{160}$, along the major axis to its outer diameter, $a_{160}$, along the minor axis can vary. Typically, this ratio is selected so that fiber 100 bends preferably in the bend plane, while cladding 100 still provides the desired mechanical support or other function(s) for which it is designed (e.g., optical function, thermal management). In some embodiments, this ratio can be relatively low, such as about 1.5:1 or less (e.g., about 1.4:1 or less, about 1.3:1 or less, about 1.2:1 or less, about 1.1:1 or less). Alternatively, in certain embodiments, this ratio can be larger than about 1.5:1 (e.g., about 1.6:1 or more, about 1.7:1 or more, about 1.8:1 or more, about 1.9:1 or more, about 2:1 or more).

The ratio of $b_{160}$ to $a_{160}$ can be characterized as an ellipticity, $\epsilon$, which is mathematically expressed as:

$$\varepsilon = \frac{(b_{160} - a_{160})}{\frac{1}{2}(b_{160} + a_{160})}.$$

Typically, $\epsilon$ is selected so that fiber 100 has desired mechanical properties. $\epsilon$ is generally sufficient large so that fiber 100 has a preferred bend plane. For example, ϵ can be about 0.05 or more (e.g., about 0.08 or more, about 0.10 or more, about 0.12 or more, about 0.15 or more, about 0.18 or more, about 0.20 or more, about 0.22 or more). ϵ should not be so large that it introduces unwanted ellipticity into other parts of the fiber, such as the core. In some embodiments, ϵ is less than 0.50 (e.g., about 0.40 or less, about 0.30 or less, about 0.25 or less, about 0.20 or less). In certain embodiments, ϵ is in a range that provides a preferred bend plane, but does not entirely prevent the fiber bending in the plane orthogonal to the preferred bend plane. ϵ can be in a range from about 0.08 to about 0.25 (e.g., from about 0.10 to about 0.20, from about 0.12 to about 0.18).

Typically, ϵ is substantially constant along the length of fiber 100. However, in certain embodiments, ϵ can vary along the length of the fiber. For example, in some embodiments, it may be desirable to have a bend plane in one section of a fiber but not in another. In such cases, ϵ can be relatively large in the section where a bend plane is desired, but small or zero in other sections. Further, in certain embodiments, a and b can be oriented differently with respect to a reference co-ordinate system for different portions of a fiber. For example, in some embodiments, it may be desirable to have a bend plane in one orientation in one section of a fiber, while having a bend plane with a different orientation at another section. This can be achieved by having a and b oriented differently in the different sections of the fiber. Vary ϵ and/or a and b orientation can be achieved introducing the asymmetry into the preform, while drawing fiber from the preform, or after the fiber has been drawn.

In some embodiments, two or more lengths of fibers having differing ϵ's and/or differing orientations of a and b may be connected to provide a concatenated fiber that has different mechanical properties along its length.

In general, the actual dimensions of $a_{160}$ and $b_{160}$ can vary depending on the operational wavelength of operation of fiber 100 and other constraints imposed by the application for which the fiber is used. For example, $a_{160}$ and $b_{160}$ should be sufficiently larger to provide adequate mechanical support and protection for core 120 and confinement region 110. However, $a_{160}$ and $b_{160}$ should be small enough so that the fiber is sufficiently flexible and/or capable in fitting in fiber conduits of a particular size (e.g., in an endoscope conduit). In some embodiments, $a_{160}$ and/or $b_{160}$ are about 500 μm or more (e.g., about 750 μm or more, about 1,000 μm or more, about 1,250 μm or more, about 1,500 μm or more, about 1,750 μm or more, about 2,000 μm or more). $a_{160}$ and/or $b_{160}$ can be about 10,000 μm or less (e.g., about 7,000 μm or less, about 5,000 μm or less, about 3,000 μm or less, about 2,000 μm or less).

Confinement region 110 includes continuous layers 130, 140, and 150 of dielectric material (e.g., polymer, glass) having different refractive indices, as opposed to multiple discrete, concentric layers that form confinement regions in other embodiments. Continuous layers 130, 140, and 150 form a spiral around an axis 199 along which the photonic crystal fiber waveguide guides electromagnetic radiation. One or more of the layers, e.g., layer 140 and/or layer 150, is a high-index layer having an index $n_H$ and a thickness $d_H$, and the layer, e.g., layer 130, is a low-index layer having an index $n_L$ and a thickness $d_L$, where $n_H > n_L$ (e.g., $n_H - n_L$ can be greater than or equal to or greater than 0.01, 0.05, 0.1, 0.2, 0.5 or more).

Because layers 130, 140, and 150 spiral around axis 199, a radial section extending from axis 199 intersects each of the layers more than once, providing a radial profile that includes alternating high index and low index layers. In some embodiments, layers 140 and 150 have the same refractive index. In such cases, for all but the innermost spiral of layer 140 and the outermost spiral of layer 150, adjacent layers 140 and 150 effectively create a single layer (e.g., a single high index or low index layer) along a radial section.

Confinement region 110 has an inner seam 121 and an outer seam 122 corresponding to the edges of the continuous layers from which the confinement region is formed. Inner seam 121 is located along an azimuth 123 that is displaced by an angle α from minor axis 162. α can be in a range from about 10° to about 170° (e.g., from about 20° to about 160°, from about 30° to about 150°, from about 40° to about 140°, from about 50° to about 130°, from about 60° to about 120°, from about 70° to about 110°, from about 80° to about 100°). In some embodiments, α is about 90°.

The inner seam does not lie in bend plane 101 of the fiber. In fiber 100, this is achieved by locating inner seam 121 away from the minor axis. Locating the inner seam away from the bend plane can be advantageous since it is believed that losses (e.g., due to scattering and/or absorption) of guided radiation is higher at the seam compared to other portions of the confinement region. Further, it is believed that the energy density of guided radiation in the core is higher towards the outside of a bend in the fiber relative to the energy density at other parts of the core. By locating the inner seam relative to the minor axis so that the seam is unlikely to lie in the bend plane (e.g., where α is about 90°), the probability that the inner seam will lie towards the outside of a fiber bend is reduced. Accordingly, the compounding effect of having a relatively high loss portion of the confinement region at the region where the energy density of guided radiation is high can be avoided, reducing the loss associated with bends in the fiber.

Although inner seam 121 and outer seam 122 are positioned at the same azimuthal position with respect to axis 199 in fiber 100, in other embodiments the inner and outer seams can be located along at different relative azimuthal positions with respect to the fiber's axis.

The spiraled layers in confinement region 110 provide a periodic variation in the index of refraction along a radial section, with a period corresponding to the optical thickness of layers 130, 140, and 150. In general, the radial periodic variation has an optical period corresponding to $n_{130}d_{130} + n_{140}d_{140} + n_{150}d_{150}$.

In embodiments where layers 140 and 150 have the same refractive index, $n_H$, and a combined thickness $d_H$, and layer 130 has a refractive index $n_L$ and thickness $d_L$, confinement region 110 has an optical period $n_H d_H + n_L d_L$. The thickness ($d_H$ and $d_L$) and optical thickness ($n_H d_H$ and $n_L d_L$) of layers 140 and 150 and of layer 140 can vary. In some embodiments, the optical $n_H d_H = n_L d_L$. Layer thickness is usually selected based on the desired optical performance of the fiber (e.g., according to the wavelength radiation to be guided). The relationship between layer thickness and optical performance is discussed below. Typically, layer thickness is in the sub-micron to tens of micron range. For example, $d_L$ and/or $d_H$ can be between about 0.1 μm to 20 μm thick (e.g., about 0.5 to 5 μm thick).

For the embodiment shown in FIG. 1, confinement region 110 is 5 optical periods thick. In practice, however, confinement region 110 may include many more optical periods (e.g., more than about 8 optical periods, 10 optical periods, 15 optical periods, 20 optical periods, 25 optical periods, such as 40 or more optical periods).

Layer 140 and 150 include a material that has a high refractive index, such as a chalcogenide glass. Layer 130 includes a material having a refractive index lower than the high index material of layers 140 and 150, and is typically mechanically flexible. For example, layer 130 often includes a polymer.

Preferably, the materials forming layers 130, 140, and 150 can be co-drawn. Criteria for selecting materials that can be co-drawn are discussed below.

In the present embodiment, core 120 is hollow. Optionally, the hollow core can be filled with a fluid, such as a gas (e.g., air, nitrogen, and/or a noble gas) or liquid (e.g., an isotropic liquid or a liquid crystal). Alternatively, core 120 can include any material or combination of materials that are rheologically compatible with the materials forming confinement region 110. In certain embodiments, core 120 can include one or more dopant materials, such as those described in U.S. patent application Ser. No. 10/121,452, entitled "HIGH INDEX-CONTRAST FIBER WAVEGUIDES AND APPLICATIONS," filed Apr. 12, 2002 and now published under Pub. No. US-2003-0044158-A1, the entire contents of which are hereby incorporated by reference.

Core and confinement regions 120 and 110 may include multiple dielectric materials having different refractive indices. In such cases, we may refer to an "average refractive index" of a given region, which refers to the sum of the weighted indices for the constituents of the region, where each index is weighted by the fractional area in the region of its constituent. The boundary between layers 130 and 140 and layers 130 and 150, however, are defined by a change in index. The change may be caused by the interface of two different dielectric materials or by different dopant concentrations in the same dielectric material (e.g., different dopant concentrations in silica).

Dielectric confinement region 110 guides EM radiation in a first range of wavelengths to propagate in dielectric core 120 along waveguide axis 199. The confinement mechanism is based on a photonic crystal structure in region 110 that forms a bandgap including the first range of wavelengths. Because the confinement mechanism is not index-guiding, it is not necessary for the core to have a higher index than that of the portion of the confinement region immediately adjacent the core. To the contrary, core 120 may have a lower average index than that of confinement region 110. For example, core 120 may be air, some other gas, such as nitrogen, or substantially evacuated. In such a case, EM radiation guided in the core will have much smaller losses and much smaller nonlinear interactions than EM radiation guided in a silica core, reflecting the smaller absorption and nonlinear interaction constants of many gases relative to silica or other such solid material. In additional embodiments, for example, core 120 may include a porous dielectric material to provide some structural support for the surrounding confinement region while still defining a core that is largely air. Accordingly, core 120 need not have a uniform index profile.

Layers 130, 140 and 150 of confinement region 110 form what is known as a Bragg fiber. The periodic optical structure of the spirally wound layers are analogous to the alternating layers of a planar dielectric stack reflector (which is also known as a Bragg mirror). The layers of confinement region 110 and the alternating planar layers of a dielectric stack reflector are both examples of a photonic crystal structure. Photonic crystal structures are described generally in *Photonic Crystals* by John D. Joannopoulos et al. (Princeton University Press, Princeton N.J., 1995).

As used herein, a photonic crystal is a dielectric structure with a refractive index modulation that produces a photonic bandgap in the photonic crystal. A photonic bandgap, as used herein, is a range of wavelengths (or inversely, frequencies) in which there are no accessible extended (i.e., propagating, non-localized) states in the dielectric structure. Typically the structure is a periodic dielectric structure, but it may also include, e.g., more complex "quasi-crystals." The bandgap can be used to confine, guide, and/or localize light by combining the photonic crystal with "defect" regions that deviate from the bandgap structure. Moreover, there are accessible extended states for wavelengths both below and above the gap, allowing light to be confined even in lower-index regions (in contrast to index-guided TIR structures, such as those described above). The term "accessible" states means those states with which coupling is not already forbidden by some symmetry or conservation law of the system. For example, in two-dimensional systems, polarization is conserved, so only states of a similar polarization need to be excluded from the bandgap. In a waveguide with uniform cross-section (such as a typical fiber), the wavevector $\beta$ is conserved, so only states with a given $\beta$ need to be excluded from the bandgap to support photonic crystal guided modes. Moreover, in a waveguide with cylindrical symmetry, the "angular momentum" index m is conserved, so only modes with the same m need to be excluded from the bandgap. In short, for high-symmetry systems the requirements for photonic bandgaps are considerably relaxed compared to "complete" bandgaps in which all states, regardless of symmetry, are excluded.

Accordingly, the dielectric stack reflector is highly reflective in the photonic bandgap because EM radiation cannot propagate through the stack. Similarly, the layers in confinement region 110 provide confinement because they are highly reflective for incident rays in the bandgap. Strictly speaking, a photonic crystal is only completely reflective in the bandgap when the index modulation in the photonic crystal has an infinite extent. Otherwise, incident radiation can "tunnel" through the photonic crystal via an evanescent mode that couples propagating modes on either side of the photonic crystal. In practice, however, the rate of such tunneling decreases exponentially with photonic crystal thickness (e.g., the number of alternating layers). It also decreases with the magnitude of the index-contrast in the confinement region.

Furthermore, a photonic bandgap may extend over only a relatively small region of propagation vectors. For example, a dielectric stack may be highly reflective for a normally incident ray and yet only partially reflective for an obliquely incident ray. A "complete photonic bandgap" is a bandgap that extends over all possible wavevectors and all polarizations. Generally, a complete photonic bandgap is only associated with a photonic crystal having index modulations along three dimensions. However, in the context of EM radiation incident on a photonic crystal from an adjacent dielectric material, we can also define an "omnidirectional photonic bandgap," which is a photonic bandgap for all possible wavevectors and polarizations for which the adjacent dielectric material supports propagating EM modes. Equivalently, an omnidirectional photonic bandgap can be defined as a photonic band gap for all EM modes above the light line, wherein the light line defines the lowest frequency propagating mode supported by the material adjacent the photonic crystal. For example, in air the light line is approximately given by $\omega = c\beta$, where $\omega$ is the angular frequency of the radiation, $\beta$ is the wavevector, and c is the speed of light. A description of an omnidirectional planar reflector is disclosed in U.S. Pat. No. 6,130,780, the contents of which are incorporated herein by reference. Furthermore, the use of alternating dielectric layers to provide omnidirectional reflection (in a planar limit) for a cylindrical waveguide geometry is disclosed in U.S. Pat. No. 6,463,200, entitled "OMNIDIRECTIONAL MULTILAYER DEVICE FOR ENHANCED OPTICAL WAVEGUIDING," to Yoel Fink et al., the contents of which are incorporated herein by reference.

When alternating the layers in confinement region 110 give rise to an omnidirectional bandgap with respect to core 120, the guided modes are strongly confined because, in principle, any EM radiation incident on the confinement region from the core is completely reflected. However, such complete reflection only occurs when there are an infinite number of layers. For a finite number of layers (e.g., about 10 optical periods), an omnidirectional photonic bandgap may correspond to a reflection in a planar geometry of at least 95% for all angles of incidence ranging from 0° to 80° and for all polarizations of EM radiation having frequency in the omnidirectional bandgap. Furthermore, even when photonic crystal fiber 100 has a confinement region with a bandgap that is not omnidirectional, it may still support a strongly guided mode, e.g., a mode with radiation losses of less than 0.1 dB/km for a range of frequencies in the bandgap. Generally, whether or not the bandgap is omnidirectional will depend on the size of the bandgap produced by the alternating layer (which generally scales with index-contrast of the two layers) and the lowest-index constituent of the photonic crystal.

In a Bragg-like configuration, the high-index layers may vary in index and thickness, and/or the low-index layers may vary in index and thickness. The confinement region may also include a periodic structure including more than three layers per period (e.g., four or more layers per period). Alternatively, in some embodiments, the confinement region can include only two layers per period. Moreover, the refractive index modulation may vary continuously or discontinuously as a function of fiber radius within the confinement region. In general, the confinement region may be based on any index modulation that creates a photonic bandgap.

In the present embodiment, multilayer structure 110 forms a Bragg reflector because it has a periodic index variation with respect to the radial axis. A suitable index variation is an approximate quarter-wave condition. It is well-known that, for normal incidence, a maximum band gap is obtained for a "quarter-wave" stack in which each layer has equal optical thickness $\lambda/4$, or equivalently $d_H/d_L = n_L/n_H$, where d and n refer to the thickness and index, respectively, of the high-index and low-index layers in a fiber including two layers per period. Normal incidence corresponds to $\beta=0$. For a cylindrical waveguide, the desired modes typically lie near the light line $\omega=c\beta$ (in the large core radius limit, the lowest-order modes are essentially plane waves propagating along z-axis, i.e., the waveguide axis). In this case, the quarter-wave condition becomes:

$$\frac{d_H}{d_L} = \frac{\sqrt{n_L^2 - 1}}{\sqrt{n_H^2 - 1}}$$

Strictly speaking, this equation may not be exactly optimal because the quarter-wave condition is modified by the cylindrical geometry, which may require the optical thickness of each layer to vary smoothly with its radial coordinate. Nonetheless, we find that this equation provides an excellent guideline for optimizing many desirable properties, especially for core radii larger than the mid-bandgap wavelength.

The radius of core 120 can vary depending on the end-use application of fiber 120. The core radius can depend on the wavelength or wavelength range of the energy to be guided by the fiber, and on whether the fiber is a single or multimode fiber. For example, where the fiber is a single mode fiber for guiding visible wavelengths (e.g., between about 400 nm and 800 nm) the core radius can be in the sub-micron to several micron range (e.g., from about 0.5 μm to 5 μm). However, where the fiber is a multimode fiber for guiding IR wavelengths (e.g., from about 2 μm to 15 μm, such as 10.6 μm), the core radius can be in the tens to thousands of microns range (e.g., from about 10 μm to about 5,000 μm, such as about 500 μm to about 2,000 μm). The core radius can be greater than about $5\lambda$ (e.g., more than about $10\lambda$, more than about $20\lambda$, more than about $30\lambda$, more than about $50\lambda$, more than about $100\lambda$), where $\lambda$ is the wavelength of the guided energy.

As discussed previously, cladding 160 provides mechanical support for confinement region 110. The thickness of cladding 160 can vary as desired along major axis 161. The thickness of cladding 160 along minor axis 162 can also vary but is generally less than the thickness along the major axis. In some embodiments, cladding 160 is substantially thicker along the major axis than confinement region 110. For example, cladding 160 can be about 10 or more times thicker than confinement region 110 (e.g., more than about 20, more than about 30, more than about 50 times thicker) along the major axis.

The composition of cladding 160 is usually selected to provide the desired mechanical support and protection for confinement region 110. In many embodiments, cladding 160 is formed from materials that can be co-drawn with the confinement region 110. Criteria for selecting materials suitable for co-drawing are discussed below. In some embodiments, cladding 160 can be formed from the same material(s) as used to form at least part of confinement region 110. For example, where layer 130 is formed from a polymer, cladding 160 can be formed from the same polymer.

Turning now to the composition of layers 130, 140 and 150 in confinement region 110, materials with a suitably high index of refraction to form a high index portion (e.g., layers 140 and 150) include chalcogenide glasses (e.g., glasses containing a chalcogen element, such as sulfur, selenium, and/or tellurium), heavy metal oxide glasses, amorphous alloys, and combinations thereof.

In addition to a chalcogen element, chalcogenide glasses may include one or more of the following elements: boron, aluminum, silicon, phosphorus, sulfur, gallium, germanium, arsenic, indium, tin, antimony, thallium, lead, bismuth, cadmium, lanthanum and the halides (fluorine, chlorine, bromide, iodine).

Chalcogenide glasses can be binary or ternary glasses, e.g., As—S, As—Se, Ge—S, Ge—Se, As—Te, Sb—Se, As—S—Se, S—Se—Te, As—Se—Te, As—S—Te, Ge—S—Te, Ge—Se—Te, Ge—S—Se, As—Ge—Se, As—Ge—Te, As—Se—Pb, As—S—Tl, As—Se—Tl, As—Te—Tl, As—Se—Ga, Ga—La—S, Ge—Sb—Se or complex, multi-component glasses based on these elements such as As—Ga—Ge—S, Pb—Ga—Ge—S, etc. The ratio of each element in a chalcogenide glass can be varied. For example, a chalcogenide glass with a suitably high refractive index may be formed with 5-30 mole % Arsenic, 20-40 mole % Germanium, and 30-60 mole % Selenium. As another example, $As_2Se_3$ can be used.

Examples of heavy metal oxide glasses with high refractive indices include $Bi_2O_3$—, PbO—, $Tl_2O_3$—, $Ta_2O_3$—, $TiO_2$—, and $TeO_2$— containing glasses.

Amorphous alloys with suitably high indices of refraction include Al—Te, R—Te(Se) (R =alkali).

Suitable materials for high and low index layers can include inorganic materials such as inorganic glasses or amorphous alloys. Examples of inorganic glasses include oxide glasses (e.g., heavy metal oxide glasses), halide glasses and/or chalcogenide glasses, and organic materials, such as polymers. Examples of polymers include acrylonitrile-butadiene-styrene (ABS), poly methylmethacrylate (PMMA), cellulose acetate butyrate (CAB), polycarbonates (PC), polystyrenes (PS) (including, e.g., copolymers styrene-butadiene (SBC), methylestyrene-acrylonitrile, styrene-xylylene, styrene-ethylene, styrene-propylene, styrene-acylonitrile (SAN)), polyetherimide (PEI), polyvinyl acetate (PVAC), polyvinyl alcohol (PVA), polyvinyl chloride (PVC), polyoxymethylene; polyformaldehyde (polyacetal) (POM), ethylene vinyl acetate copolymer (EVAC), polyamide (PA), polyethylene terephthalate (PETP), fluoropolymers (including, e.g., polytetrafluoroethylene (PTFE), polyperfluoroalkoxythylene (PFA), fluorinated ethylene propylene (FEP)), polybutylene terephthalate (PBTP), low density polyethylene (PE), polypropylene (PP), poly methyl pentenes (PMP) (and other polyolefins, including cyclic polyolefins), polytetrafluoroethylene (PTFE), polysulfides (including, e.g., polyphenylene sulfide (PPS)), and polysulfones (including, e.g., polysulfone (PSU), polyehtersulfone (PES), polyphenylsulphone (PPSU), polyarylalkylsulfone, and polysulfonates). Polymers can be homopolymers or copolymers (e.g., (Co)poly(acrylamide-acrylonitrile) and/or acrylonitrile styrene copolymers). Polymers can include polymer blends, such as blends of polyamides-polyolefins, polyamides-polycarbonates, and/or PES-polyolefins, for example.

Further examples of polymers that can be used include cyclic olefin polymers (COPs) and cyclic olefin copolymers (COCs). In some embodiments, COPs and COCs can be prepared by polymerizing norbornen monomers or copolymerization norbornen monomers and other polyolefins (polyethylene, polypropylene). Commercially-available COPs and/or COCs can be used, including, for example, Zeonex® polymers (e.g., Zeonex® E48R) and Zeonor® copolymers (e.g., Zeonor® 1600), both available from Zeon Chemicals L.P. (Louisville, Ky.). COCs can also be obtained from Promerus LLC (Brecksville, Ohio) (e.g., such as FS1700).

Suitable oxide glasses may include glasses that contain one or more of the following compounds: 0-40 mole % of $M_2O$ where M is Li, Na, K, Rb, or Cs; 0-40 mole % of M'O where M' is Mg, Ca, Sr, Ba, Zn, or Pb; 0-40 mole % of $M''_2O_3$ where M" is B, Al, Ga, In, Sn, or Bi; 0-60 mole % $P_2O_5$; and 0-40 mole % $SiO_2$.

Portions of photonic crystal fiber waveguides (e.g., layers in confinement region 110) can optionally include other materials. For example, any portion can include one or more materials that change the index of refraction of the portion. A portion can include a material that increases the refractive index of the portion. Such materials include, for example, germanium oxide, which can increase the refractive index of a portion containing a borosilicate glass. Alternatively, a portion can include a material that decreases the refractive index of the portion. For example, boron oxide can decrease the refractive index of a portion containing a borosilicate glass.

Portions of photonic crystal fiber waveguides can be homogeneous or inhomogeneous. For example, one or more portions can include nano-particles (e.g., particles sufficiently small to minimally scatter light at guided wavelengths) of one material embedded in a host material to form an inhomogeneous portion. An example of this is a high-index polymer composite formed by embedding a high-index chalcogenide glass nano-particles in a polymer host. Further examples include CdSe and or PbSe nano-particles in an inorganic glass matrix.

Portions of photonic crystal fiber waveguides can include materials that alter the mechanical, rheological and/or thermodynamic behavior of those portions of the fiber. For example, one or more of the portions can include a plasticizer. Portions may include materials that suppress crystallization, or other undesirable phase behavior within the fiber. For example, crystallization in polymers may be suppressed by including a cross-linking agent (e.g., a photosensitive cross-linking agent). In other examples, if a glass-ceramic material was desired, a nucleating agent, such as $TiO_2$ or $ZrO_2$, can be included in the material.

Portions can also include compounds designed to affect the interface between adjacent portions in the fiber (e.g., between the low index and high index layers). Such compounds include adhesion promoters and compatibilizers. For example, an organo-silane compound can be used to promote adhesion between a silica-based glass portion and a polymer portion. For example, phosphorus or $P_2O_5$ is compatible with both chalcogenide and oxide glasses, and may promote adhesion between portions formed from these glasses.

Fiber waveguides can include additional materials specific to particular fiber waveguide applications. In fiber amplifiers, for example, any of the portions can be formed of any dopant or combination of dopants capable of interacting with an optical signal in the fiber to enhance absorption or emission of one or more wavelengths of light by the fiber, e.g., at least one rare earth ion, such as erbium ions, ytterbium ions neodymium ions, holmium ions, dysprosium ions, and/or thulium ions.

Portions of high index-contrast waveguides can include one or more nonlinear materials. Nonlinear materials are materials that enhance the nonlinear response of the waveguide. In particular, nonlinear materials have a larger nonlinear response than silica. For example, nonlinear materials have a Kerr nonlinear index, $n^{(2)}$, larger than the Kerr nonlinear index of silica (i.e., greater than $3.5 \times 10^{-20}$ $m^2/W$, such as greater than $5 \times 10^{-20}$ $m^2/W$, greater than $10 \times 10^{-20}$ $m^2/W$, greater than $20 \times 10^{-20}$ $m^2/W$, greater than $100 \times 10^{-20}$ $m^2/W$, greater than $200 \times 10^{-20}$ $m^2/W$).

When making a robust fiber waveguides using a drawing process, not every combination of materials with desired optical properties is necessarily suitable. Typically, one should select materials that are rheologically, thermo-mechanically, and physico-chemically compatible. Several criteria for selecting compatible materials will now be discussed.

A first criterion is to select materials that are rheologically compatible. In other words, one should select materials that have similar viscosities over a broad temperature range, corresponding to the temperatures experience during the different stages of fiber drawing and operation. Viscosity is the resistance of a fluid to flow under an applied shear stress. Here, viscosities are quoted in units of Poise. Before elaborating on rheological compatibility, it is useful define a set of characteristic temperatures for a given material, which are temperatures at which the given material has a specific viscosity.

The annealing point, $T_a$, is the temperature at which a material has a viscosity $10^{13}$ Poise. $T_a$ can be measured using a Model SP-2A System from Orton Ceramic Foundation (Westerville, Ohio). Typically, $T_a$ is the temperature at which the viscosity of a piece of glass is low enough to allow for relief of residual stresses.

The softening point, $T_s$, is the temperature at which a material has a viscosity $10^{7.65}$ Poise. $T_s$ can be measured using a softening point instrument, e.g., Model SP-3A from Orton Ceramic Foundation (Westerville, Ohio). The softening point is related to the temperature at which the materials flow changes from plastic to viscous in nature.

The working point, $T_w$, is the temperature at which a material has a viscosity $10^4$ Poise. $T_w$ can be measured using a glass viscometer, e.g., Model SP-4A from Orton Ceramic Foundation (Westerville, Ohio). The working point is related to the temperature at which a glass can be easily drawn into a fiber. In some embodiments, for example, where the material is an inorganic glass, the material's working point temperature can be greater than 250° C., such as about 300° C., 400° C., 500° C. or more.

The melting point, $T_m$, is the temperature at which a material has a viscosity $10^2$ Poise. $T_m$ can also be measured using a glass viscometer, e.g., Model SP-4A from Orton Ceramic Foundation (Westerville, Ohio). The melting point is related to the temperature at which a glass becomes a liquid and control of the fiber drawing process with respect to geometrical maintenance of the fiber becomes very difficult.

To be rheologically compatible, two materials should have similar viscosities over a broad temperature range, e.g., from the temperature at which the fiber is drawn down to the temperature at which the fiber can no longer release stress at a discernible rates (e.g., at $T_a$) or lower. Accordingly, the working temperature of two compatible materials should be similar, so that the two materials flow at similar rates when drawn. For example, if one measures the viscosity of the first material, $\eta_1(T)$ at the working temperature of the second material, $T_{w2}$, $\eta_1(T_{w2})$ should be at least $10^3$ Poise, e.g., $10^4$ Poise or $10^5$ Poise, and no more than $10^6$ Poise. Moreover, as the drawn fiber cools the behavior of both materials should change from viscous to elastic at similar temperatures. In other words, the softening temperature of the two materials should be similar. For example, at the softening temperature of the second material, $T_{s2}$, the viscosity of the first material, $\eta_1(T_{s2})$ should be at least $10^6$ Poise, e.g., $10^7$ Poise or $10^8$ Poise and no more than $10^9$ Poise. In preferred embodiments, it should be possible to anneal both materials together, so at the annealing temperature of the second material, $T_{a2}$, the viscosity of the first material, $\eta_1(T_{a2})$ should be at least $10^8$ Poise (e.g., at least $10^9$ Poise, at least $10^{10}$ Poise, at least $10^{11}$ Poise, at least $10^{12}$ Poise, at least $10^{13}$ Poise, at least $10^{14}$ Poise).

Additionally, to be rheologically compatible, the change in viscosity as a function of temperature (i.e., the viscosity slope) for both materials should preferably match as close as possible.

A second selection criterion is that the thermal expansion coefficients (TEC) of each material should be similar at temperatures between the annealing temperatures and room temperature. In other words, as the fiber cools and its rheology changes from liquid-like to solid-like, both materials' volume should change by similar amounts. If the two materials TEC's are not sufficiently matched, a large differential volume change between two fiber portions can result in a large amount of residual stress buildup, which can cause one or more portions to crack and/or delaminate. Residual stress may also cause delayed fracture even at stresses well below the material's fracture stress.

The TEC is a measure of the fractional change in sample length with a change in temperature. This parameter can be calculated for a given material from the slope of a temperature-length (or equivalently, temperature-volume) curve. The temperature-length curve of a material can be measured using e.g., a dilatometer, such as a Model 1200D dilatometer from Orton Ceramic Foundation (Westerville, Ohio). The TEC can be measured either over a chosen temperature range or as the instantaneous change at a given temperature. This quantity has the units $°C.^{-1}$.

For many materials, there are two linear regions in the temperature-length curve that have different slopes. There is a transition region where the curve changes from the first to the second linear region. This region is associated with a glass transition, where the behavior of a glass sample transitions from that normally associated with a solid material to that normally associated with a viscous fluid. This is a continuous transition and is characterized by a gradual change in the slope of the temperature-volume curve as opposed to a discontinuous change in slope. A glass transition temperature, $T_g$, can be defined as the temperature at which the extrapolated glass solid and viscous fluid lines intersect. The glass transition temperature is a temperature associated with a change in the materials rheology from a brittle solid to a solid that can flow. Physically, the glass transition temperature is related to the thermal energy required to excite various molecular translational and rotational modes in the material. The glass transition temperature is often taken as the approximate annealing point, where the viscosity is $10^{13}$ Poise, but in fact, the measured $T_g$ is a relative value and is dependent upon the measurement technique.

A dilatometer can also be used to measure a dilatometric softening point, $T_{ds}$. A dilatometer works by exerting a small compressive load on a sample and heating the sample. When the sample temperature becomes sufficiently high, the material starts to soften and the compressive load causes a deflection in the sample, when is observed as a decrease in volume or length. This relative value is called the dilatometric softening point and usually occurs when the materials viscosity is between $10^{10}$ and $10^{12.5}$ Poise. The exact $T_{ds}$ value for a material is usually dependent upon the instrument and measurement parameters. When similar instruments and measurement parameters are used, this temperature provides a useful measure of different materials rheological compatibility in this viscosity regime.

As mentioned above, matching the TEC is an important consideration for obtaining fiber that is free from excessive residual stress, which can develop in the fiber during the draw process. Typically, when the TEC's of the two materials are not sufficiently matched, residual stress arises as elastic stress. The elastic stress component stems from the difference in volume contraction between different materials in the fiber as it cools from the glass transition temperature to room temperature (e.g., 25° C.). The volume change is determined by the TEC and the change in temperature. For embodiments in which the materials in the fiber become fused or bonded at any interface during the draw process, a difference in their respective TEC's will result in stress at the interface. One material will be in tension (positive stress) and the other in compression (negative stress), so that the total stress is zero. Moderate compressive stresses themselves are not usually a major concern for glass fibers, but tensile stresses are undesirable and may lead to failure over time. Hence, it is desirable to minimize the difference in TEC's of component materials to minimize elastic stress generation in a fiber during drawing. For example, in a composite fiber formed from two different materials, the absolute difference between the TEC's of each glass between $T_g$ and room temperature measured with a dilatometer with a heating rate of 3° C./min, should be no more than $5 \times 10^{-6}$ $°C.^{-1}$ (e.g., no more than $4 \times 10^{-6}$ $°C.^{-1}$, no more than $3 \times 10^{-6}$ $°C.^{-1}$, no more than $2 \times 10^{-6}$ $°C.^{-1}$, no more than $1 \times 10^{-6}$ $°C.^{-1}$, no more than $5 \times 10^{-7}$ $°C.^{-1}$, no more than $4 \times 10^{-7}$ $°C.^{-1}$, no more than $3 \times 10^{-7}$ $°C.^{-1}$, no more than $2 \times 10^{-7}$ $°C.^{-1}$).

While selecting materials having similar TEC's can minimize an elastic stress component, residual stress can also develop from viscoelastic stress components. A viscoelastic stress component arises when there is sufficient difference between strain point or glass transition temperatures of the component materials. As a material cools below $T_g$ it undergoes a sizeable volume contraction. As the viscosity changes in this transition upon cooling, the time needed to relax stress increases from zero (instantaneous) to minutes. For example, consider a composite preform made of a glass and a polymer having different glass transition ranges (and different $T_g$'s). During initial drawing, the glass and polymer behave as viscous fluids and stresses due to drawing strain are relaxed instantly. After leaving the hottest part of the draw furnace, the fiber rapidly loses heat, causing the viscosities of the fiber materials to increase exponentially, along with the stress relaxation time. Upon cooling to its $T_g$, the glass and polymer cannot practically release any more stress since the stress relaxation time has become very large compared with the draw rate. So, assuming the component materials possess different $T_g$ values, the first material to cool to its $T_g$ can no longer reduce stress, while the second material is still above its $T_g$ and can release stress developed between the materials. Once the second material cools to its $T_g$, stresses that arise between the materials can no longer be effectively relaxed. Moreover, at this point the volume contraction of the second glass is much greater than the volume contraction of the first material (which is now below its $T_g$ and behaving as a brittle solid). Such a situation can result sufficient stress buildup between the glass and polymer so that one or both of the portions mechanically fail. This leads us to a third selection criterion for choosing fiber materials: it is desirable to minimize the difference in $T_g$'s of component materials to minimize viscoelastic stress generation in a fiber during drawing. Preferably, the glass transition temperature of a first material, $T_{g1}$, should be within 100° C. of the glass transition temperature of a second material, $T_{g2}$ (e.g., $|T_{g1}-T_{g2}|$ should be less than 90° C., less than 80° C., less than 70° C., less than 60° C., less than 50° C., less than 40° C., less than 30° C., less than 20° C., less than 10° C.).

Since there are two mechanisms (i.e., elastic and viscoelastic) to develop permanent stress in drawn fibers due to differences between constituent materials, these mechanisms may be employed to offset one another. For example, materials constituting a fiber may naturally offset the stress caused by thermal expansion mismatch if mismatch in the materials $T_g$'s results in stress of the opposite sign. Conversely, a greater difference in $T_g$ between materials is acceptable if the materials' thermal expansion will reduce the overall permanent stress. One way to assess the combined effect of thermal expansion and glass transition temperature difference is to compare each component materials' temperature-length curve. After finding $T_g$ for each material using the foregoing slope-tangent method, one of the curves is displaced along the ordinate axis such that the curves coincide at the lower $T_g$ temperature value. The difference in y-axis intercepts at room temperature yields the strain, $\epsilon$, expected if the glasses were not conjoined. The expected tensile stress, $\sigma$, for the material showing the greater amount of contraction over the temperature range from $T_g$ to room temperature, can be computed simply from the following equation:

$$\sigma = E \cdot \epsilon,$$

where E is the elastic modulus for that material. Typically, residual stress values less than 100 MPa (e.g., less than 50 MPa, less than 30 MPa), are sufficiently small to indicate that two materials are compatible.

A fourth selection criterion is to match the thermal stability of candidate materials. A measure of the thermal stability is given by the temperature interval $(T_x-T_g)$, where $T_x$ is the temperature at the onset of the crystallization as a material cools slowly enough that each molecule can find its lowest energy state. Accordingly, a crystalline phase is a more energetically favorable state for a material than a glassy phase. However, a material's glassy phase typically has performance and/or manufacturing advantages over the crystalline phase when it comes to fiber waveguide applications. The closer the crystallization temperature is to the glass transition temperature, the more likely the material is to crystallize during drawing, which can be detrimental to the fiber (e.g., by introducing optical inhomogeneities into the fiber, which can increase transmission losses). Usually a thermal stability interval, $(T_x-T_g)$ of at least about 80° C. (e.g., at least about 100° C.) is sufficient to permit fiberization of a material by drawing fiber from a preform. In preferred embodiments, the thermal stability interval is at least about 120° C., such as about 150° C. or more, such as about 200° C. or more. $T_x$ can be measured using a thermal analysis instrument, such as a differential thermal analyzer (DTA) or a differential scanning calorimeter (DSC).

A further consideration when selecting materials that can be co-drawn are the materials' melting temperatures, $T_m$. At the melting temperature, the viscosity of the material becomes too low to successfully maintain precise geometries during the fiber draw process. Accordingly, in preferred embodiments the melting temperature of one material is higher than the working temperature of a second, rheologically compatible material. In other words, when heating a preform, the preform reaches a temperature at it can be successfully drawn before either material in the preform melts.

One example of a pair of materials which can be co-drawn and which provide a photonic crystal fiber waveguide with high index contrast between layers of the confinement region are $As_2Se_3$ and the polymer PES. $As_2Se_3$ has a glass transition temperature ($T_g$) of about 180° C. and a thermal expansion coefficient (TEC) of about $24 \times 10^{-6}$/° C. At 10.6 µm, $As_2Se_3$ has a refractive index of 2.7775, as measured by Hartouni and coworkers and described in *Proc. SPIE*, 505, 11 (1984), and an absorption coefficient, $\alpha$, of 5.8 dB/m, as measured by Voigt and Linke and described in "Physics and Applications of Non-Crystalline Semiconductors in Optoelectronics," Ed. A. Andriesh and M. Bertolotti, NATO ASI Series, 3. High Technology, Vol. 36, p. 155 (1996). Both of these references are hereby incorporated by reference in their entirety. PES has a TEC of about $55 \times 10^{-6}$/° C. and has a refractive index of about 1.65.

In some embodiments, photonic crystal fibers, such as fiber 100, can be made by rolling a planar multilayer article into a spiral structure and drawing a fiber from a preform derived from the spiral structure.

Figure 2A:
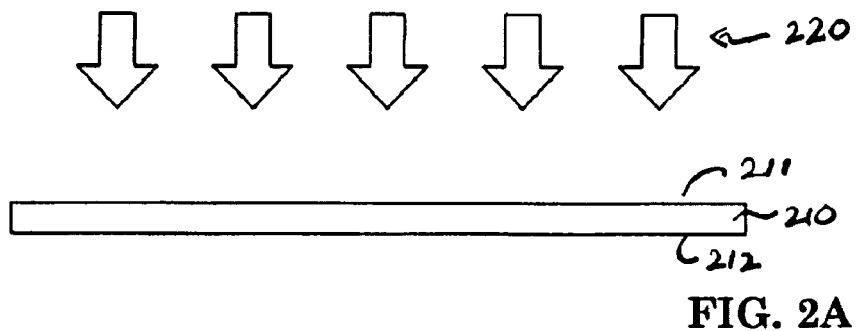
FIGS. 2A-2E are schematic diagrams showing stages in a method for forming the photonic crystal fiber shown in FIG. 1.
Figure 2B:
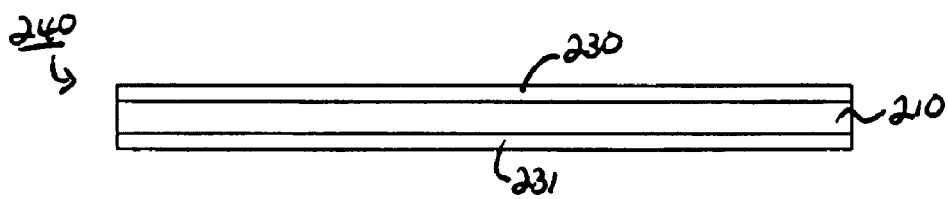

Referring to FIG. 2A, to prepare a preform, one or more glasses are deposited 220 on opposing surfaces 211 and 212 of a polymer film 210. The glass can be deposited by methods including thermal evaporation, chemical vapor deposition, or sputtering. Referring to FIG. 2B, the deposition process provides a multilayer article 240 composed of layers 230 and 231 of glass on polymer film 210.

Figure 2C:
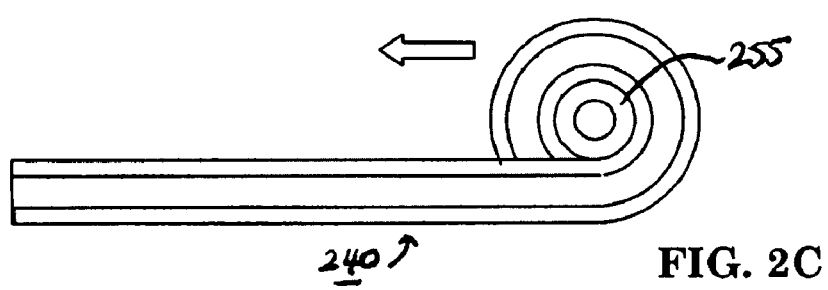
Figures 2D, 2E:
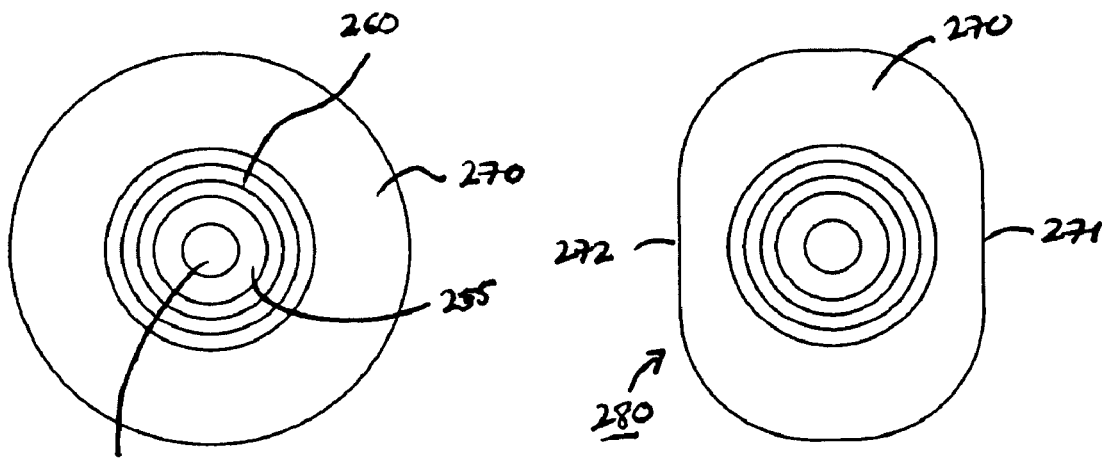

Referring to FIG. 2C, following the deposition step, multilayer film 240 is rolled around a mandrel 255 (e.g., a hollow glass, such as a borosilicate glass, or polymer tube) to form a spiral tube. A number (e.g., about three to ten) of polymer films are then wrapped around the spiral tube to form a preform wrap. In some embodiments, the polymer films are made from the same polymer or glass used to form multilayer article. Under vacuum, the preform wrap is heated to a temperature above the glass transition temperature of the polymer(s) and glass(es) forming multilayer film 240 and the films wrapped around the spiral tube. The preform wrap is heated for sufficient time for the layers of the spiral tube to fuse to each other and for the spiral tube to fuse to polymer films wrapped around it. The temperature and length of time of heating depends on the preform wrap composition. Where the multilayer is composed of $As_2Se_3$ and PES and the wrapping films are composed of PES, for example, heating for 15-20 minutes (e.g., about 18 minutes) at about 200-300° C. (e.g., about 250° C.) is typically sufficient. The heating fuses the various layers to each other, consolidating the spiral tube and wrapping films. The consolidated structure is shown in FIG. 2D. The spiral tube consolidates to a multilayer region 260 corresponding to rolled multilayer film 240. The wrapped polymer films consolidate to a monolithic support cladding 270. The consolidated structure retains a hollow core 250 of mandrel 255.

As an alternative to wrapping polymer films around the spiral tube to provide support cladding 270, the spiral tube can be inserted into a hollow tube with inner diameter matching the outer diameter of the spiral tube.

Referring to FIG. 2E, portions at opposing sides 271 and 272 of cladding 270 are removed to provide a perform 280 having an asymmetric cross-sectional shape. The portions can be removed by cutting or shaving the perform (e.g., with a blade or milling cutter) or by grinding (e.g., with a grinding wheel) and polishing the sides of the perform.

Mandrel 255 is removed from the consolidated structure to provide a hollow preform that is then drawn into a fiber. The preform has the same composition and relative dimensions (e.g., core radius to thickness of layers in the confinement region) of the final fiber. The absolute dimensions of the fiber depend on the draw ratio used. Long lengths of fiber can be drawn (e.g., up to thousands of meters). The drawn fiber can then be cut to the desired length.

Preferably, consolidation occurs at temperatures below the glass transition for the mandrel so that the mandrel provides a rigid support for the spiral tube. This ensures that the multilayer film does not collapse on itself under the vacuum. The mandrel's composition can be selected so that it releases from the innermost layer of the multilayer tube after consolidation. Alternatively, where the mandrel adheres to the innermost layer of the multilayer tube during consolidation, it can be removed chemically, e.g., by etching. For example, in embodiments where the mandrel is a glass capillary tube, it can be etched, e.g., using hydrofluoric acid, to yield the preform.

In embodiments where a solid core is desired, the multilayer tube can be consolidated around a solid mandrel that is co-drawn with the other parts of the fiber. Alternatively, in other embodiments, the multilayer film can be rolled without a mandrel to provide a self-supporting spiral tube.

In some embodiments, the fiber asymmetry can be introduced after the fiber is drawn from a perform. For example, a fiber can be shaved or ground as part of the production process after being drawn but before being spooled. In certain embodiments, the preform can be shaved, and then the fiber can be shaved further after it has been drawn.

Photonic crystal fiber waveguides prepared using the previously discussed technique can be made with a low defect density. For example, waveguides can have less than about one defect per 5 meters of fiber (e.g., less than about one defect per 10 meters, 20 meters, 50 meters, 100 meters of fiber). Defects include both material defects (e.g., impurities) and structural defects (e.g., delamination between layers, cracks with layers), both of which can scatter guided radiation from the core resulting in signal loss and can cause local heating of the fiber. Accordingly, reducing fiber defects is desirable in applications sensitive to signal loss (e.g., in high power applications where radiation absorbed by the fiber can cause damage to the fiber).

Figure 3:
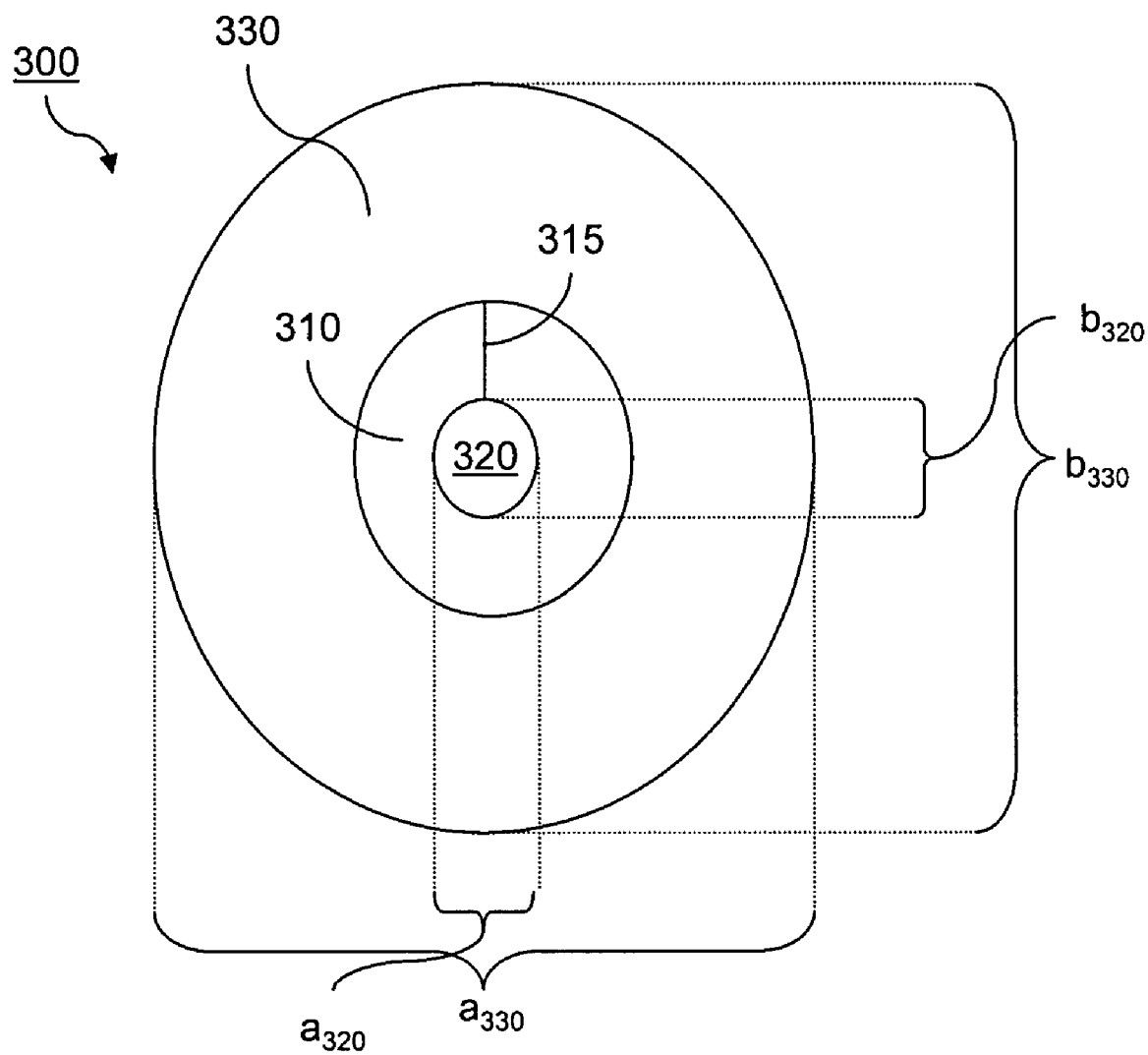
FIG. 3 is a cross-sectional view of an embodiment of a photonic crystal fiber.

In fiber 100, only the outer surface of the cladding has an asymmetric cross-section. More generally, however, other portions of photonic crystal fibers can have an asymmetric cross-section. In certain embodiments, the confinement region and/or core can also have an asymmetric cross-section. For example, referring to FIG. 3, a photonic crystal fiber 300 has a confinement region 310 having an asymmetric cross-section surrounded by an asymmetric cladding 330. The core 320 of fiber 300 also has an asymmetric cross-section. Confinement region 310, core 320, and cladding 330 have an elliptical cross-sectional shape. The confinement region includes an inner seam 315 that is located on the major axis of the ellipse, although, more generally, the inner seam can be located at other orientations with respect to the elliptical axes.

In some embodiments, the asymmetry of the core and/or confinement region can affect the guiding properties of the fiber. For example, in certain embodiments, asymmetric fibers can maintain the polarization state of guided radiation (i.e., can be polarization maintaining fibers).

Cladding 330 and core 320 have dimensions $b_{330}$ and $b_{320}$, respectively, along the major axis. Correspondingly, cladding 330 and core 320 have dimensions $a_{330}$ and $a_{320}$ along the minor axis. Respective ellipticities for the cladding and core can be expressed mathematically as:

$$\varepsilon_{330} = \frac{(b_{330} - a_{330})}{\frac{1}{2}(b_{330} - a_{330})},$$

and $$\varepsilon_{320} = \frac{(b_{320} - a_{320})}{\frac{1}{2}(b_{320} - a_{320})}.$$

In general, $\varepsilon_{330}$ and $\varepsilon_{320}$ can be the same or different. In some embodiments, $\varepsilon_{320} > \varepsilon_{330}$. For example, in embodiments where an asymmetric core is desired, such as in a polarization-maintaining fiber, a high core ellipticity may be desired. Alternatively, in other embodiments, $\varepsilon_{330} > \varepsilon_{320}$.

Fiber 300 can be made by applying a force (e.g., a compressive force) to opposing sides of the fiber or fiber perform. The force can be applied while the fiber or perform is at an elevated temperature (e.g., at a temperature where components of the fiber have a softened) to facilitate the deformation. The deformation sets once the fiber or fiber perform cools.

Furthermore, while fiber 300 has an elliptical cross-sectional shape, and fiber 100 has a shape composed of two circular arcs and two straight lines, in general, fibers can have other shapes. For example, fibers can have asymmetric polygonal shapes, can be formed from arcuate portions having different radii of curvature, and/or from arcuate portions that curve in opposite directions. Generally, the shape should provide the fiber with a preferred bending plane.

While the foregoing fibers are asymmetric with respect to their cross-sectional shape, in general, fibers can be asymmetric in a variety of ways in order to provide a preferred bend plane. For example, in some embodiments, fibers can include material asymmetries that give rise to a preferred bend plane. Material asymmetries refer to variations between the material properties of different portions of a fiber that cause the fiber to bend preferably in a particular way. For example, a portion of a fiber cladding can be formed from a material that is mechanically less rigid that other portions, causing the fiber to bend preferably at that portion. Mechanical variations can be caused by compositional changes or by physical differences in portions having the same composition. Compositional differences can be introduced, e.g., by doping portions of a fiber or fiber preform with a dopant that alters the mechanical properties of a fiber. As another example, compositional differences can be introduced by forming different portions of a fiber from different compounds. Physical differences refer to, e.g., differences in the degree of crystallinity in different portions of a fiber. Physical differences, such as differences in crystallinity, can be introduced by selectively heating and/or cooling portions of a fiber during fiber fabrication, and/or using different rates of heating/cooling on different fiber portions.

Figure 4A:
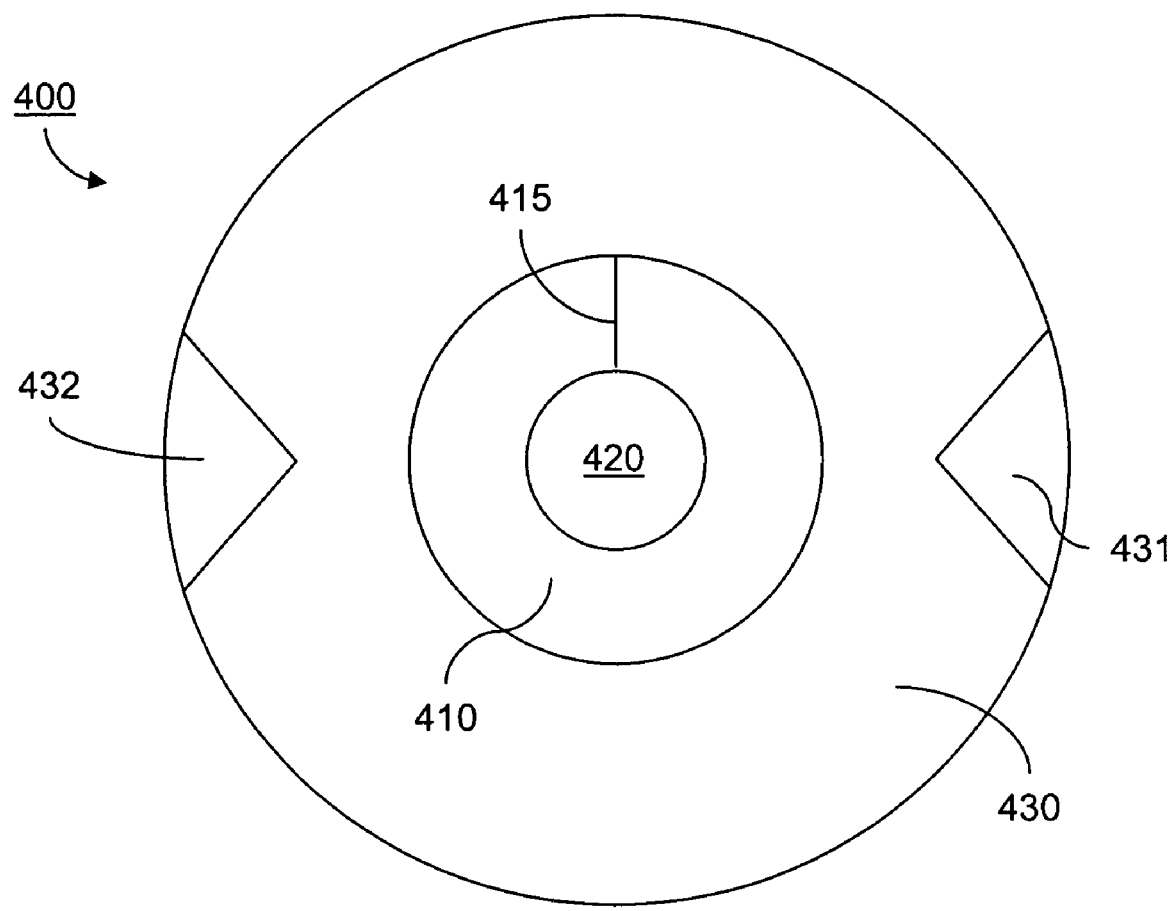
FIGS. 4A-4D are cross-sectional views of embodiments of photonic crystal fibers.

Referring to FIG. 4A, another example of a photonic crystal 400 includes a confinement region 410 surrounding a core 420, and a cladding 430 surrounding confinement region 410. Confinement region 410 includes a seam 415. Cladding 430 includes two portions 431 and 432 that are composed of different materials than the rest of the cladding. For example, in some embodiments, portions 431 and 432 are formed from a material that has a higher mechanical stiffness than the rest of cladding 430. As an example, portions 431 and 432 can be formed from a polymer that has a higher density of cross-linking than a polymer forming the rest of cladding 430. In embodiments where portions 431 and 433 are stiffer than the rest of the cladding, fiber 400 includes a preferred bend plane that is perpendicular to the plane that includes a diameter that intersects portions 431 and 432. Alternatively, in certain embodiments, portions 431 and 432 are formed from materials that are less stiff than the material forming the rest of cladding 430. In such cases, fiber 400 has a preferred bend plane that corresponds to the plane that includes a diameter that intersects portions 431 and 432. Portions 431 and 432 can run substantially along the entire length of fiber 400, or just along segments of the fiber.

Figure 4B:
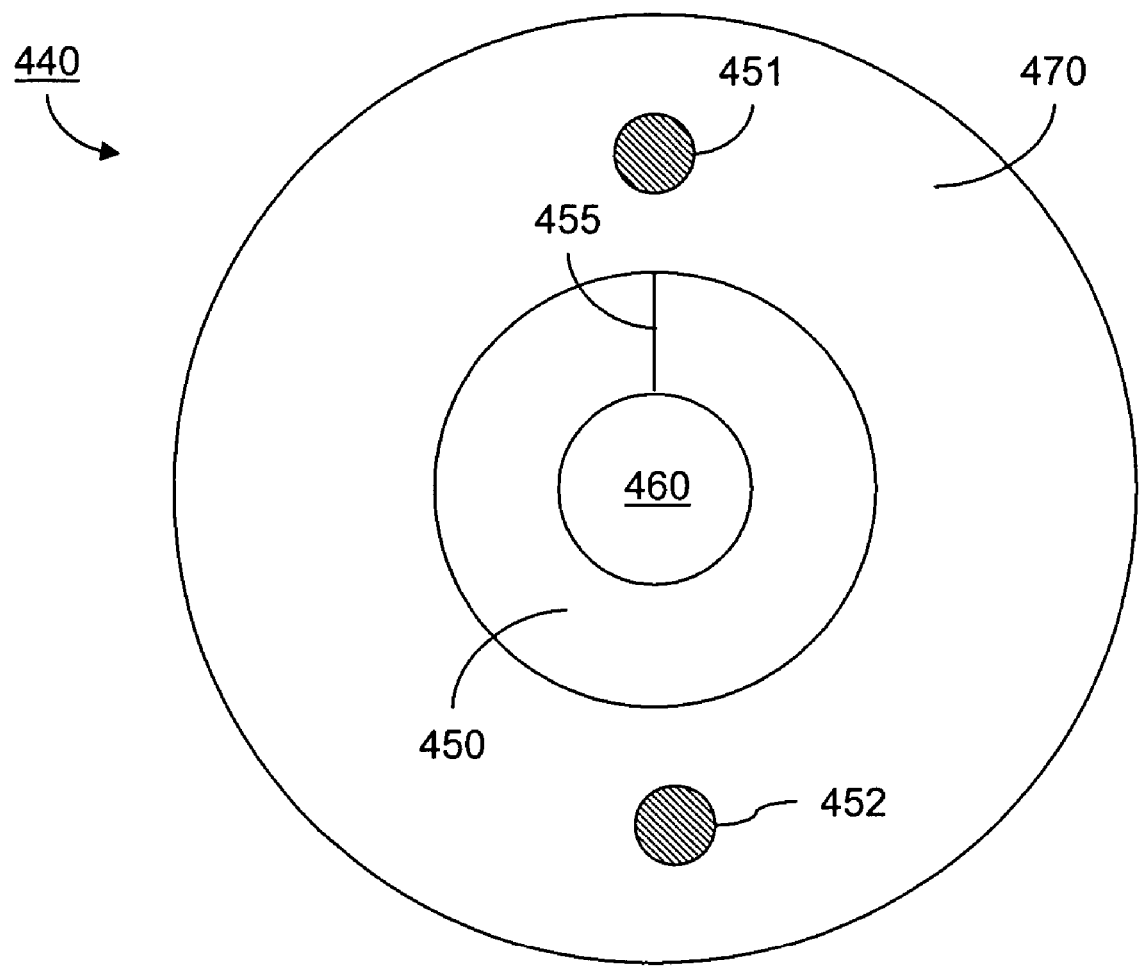

Referring to FIG. 4B, a further example of a photonic crystal fiber 440 includes a confinement region 450 surrounding a core 460. A cladding 470 surrounds confinement region 450. Confinement region 460 includes a seam 455. Embedded in cladding 470 are two stiffening elements 451 and 452, which are formed from materials having higher mechanical stiffness than the rest of cladding 470. For example, stiffening elements 451 and 452 can be formed from wires (e.g., steel wires) that are inserted into holes that run the length of fiber 440. As an example, forming photonic crystal fiber can include machining grooves into the preform cladding on opposite sides of the preform core. The fiber is drawn at a temperature and tension such that the grooves are preserved in the drawn fiber. Finally, wires are inserted into the grooves and an adhesive (e.g., an epoxy) is used to fix the wires in place.

Stiffening elements 451 and 452 create a bend plane orthogonal to the diagonal connecting the two stiffening elements. Other embodiments can include more than two stiffening elements. Further, in certain embodiments, claddings can included embedded elements that are of lower mechanical stiffness than the rest of the cladding, providing a bend plane in the same plane as the diagonal intersecting the elements. For example, a cladding can include two or more holes that run along the length of the fiber.

Figure 4C:
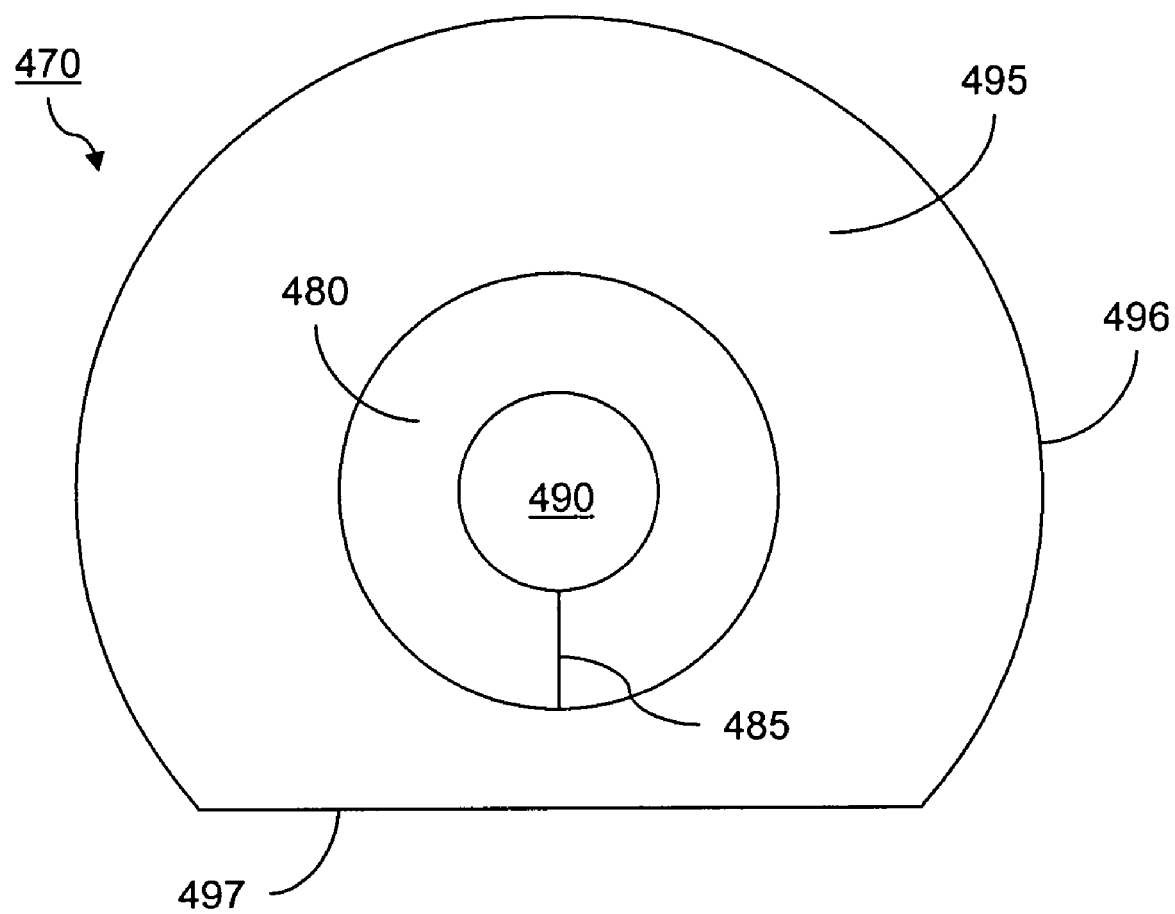

In some embodiments, asymmetry can be introduced on one side of the fiber only, rather than on opposing sides as for the embodiments described above. For example, referring to FIG. 4C, a photonic crystal fiber 470 includes a confinement region 480 that surrounds a core 490. Confinement region 480 includes a seam 485. Confinement region 480 is surrounded by a cladding 495, that, in cross-section, includes a circular portion 496 and a flat portion 497. Flat portion 497 can be formed by shaving or grinding the fiber or fiber preform on one side only. Flat portion 497 is positioned so that seam 485 lies between it and core 490 in a radial direction from the fiber axis. Fiber 470 has a bend plane that intersects portion 497. Moreover, fiber 470 bends preferably so that seam 385 is on the inside of the bend.

Figure 4D:
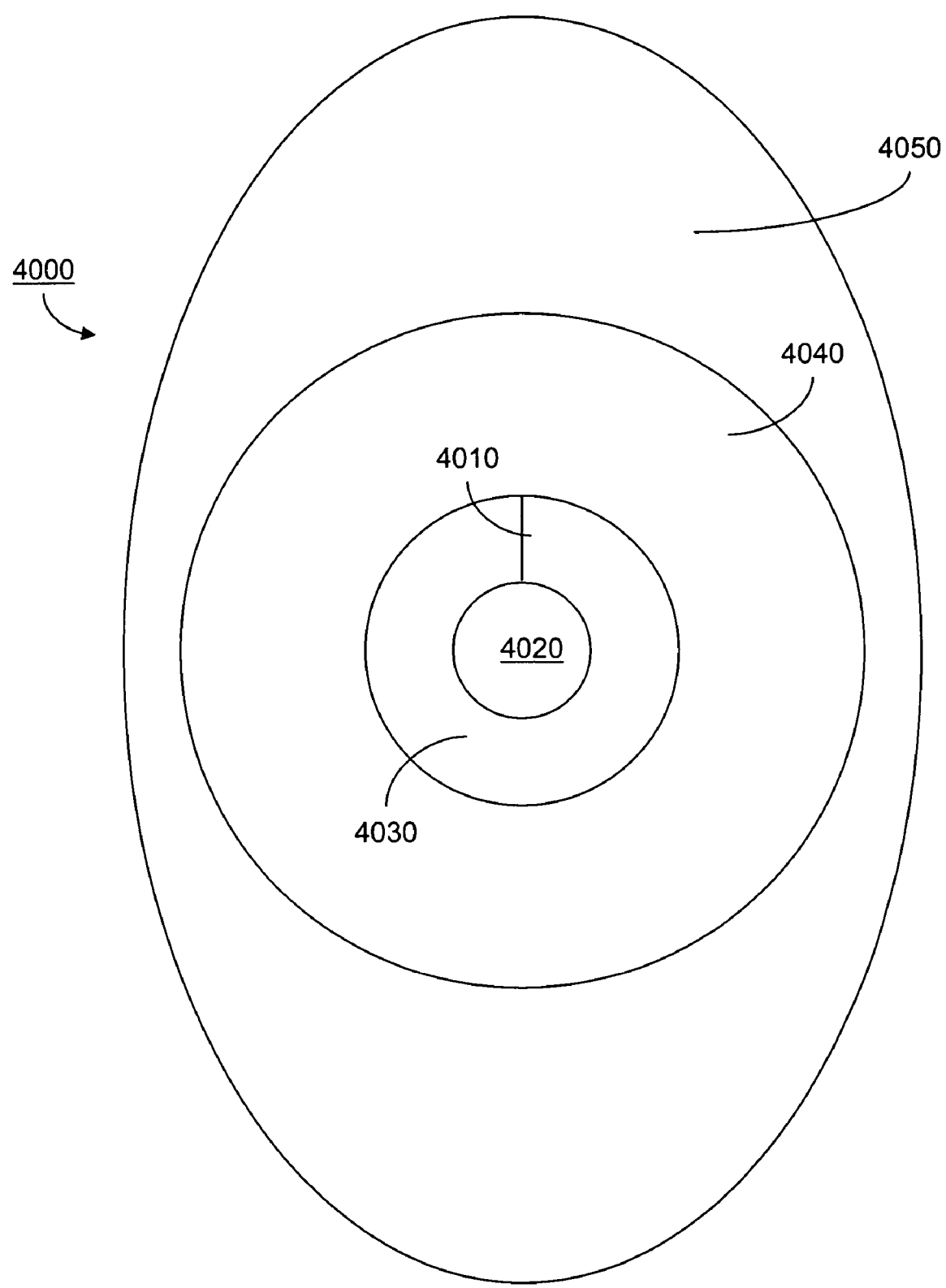

In some embodiments, fibers can include a symmetric first cladding, but can include additional structure outside of the cladding that cause the fiber to bend preferably in a particular plane. For example, fibers can be placed in one or more jackets that are asymmetric when it comes to allowing the fiber to bend. Referring to FIG. 4D, for example, a photonic crystal fiber includes a jacket 4050 that surrounds a cladding 4040. Cladding 4040, in turn, surrounds, a confinement region 4030, which surrounds a core 4020. Confinement region 4030 includes a seam 4010. Jacket 4050 has an elliptical cross-section that provides a bend plane. Cladding 4040 has a circular cross-section. In certain embodiments, cladding 4040, confinement region 4030, and core 4020 are formed by drawing a preform structure. The drawn fiber is then inserted into a hole in jacket 4050. The orientation of the jacket with respect to the rest of the fiber can be secured by, for example, applying an adhesive to the interface of the jacket and the cladding, or by consolidating the jacket onto the cladding (e.g., using heat).

Although the fibers described above include confinement regions that have a seam, in general, embodiments of fibers with a bend plane can be designed to position other features in or away from the bend plane. For example, in some embodiments, fibers can include extended defects (e.g., structural or compositional defects) other than a seam that is desirably positioned away from the bend plane. Moreover, embodiments can include confinement regions with no seams (e.g., confinement regions that are formed from a number of annular layers).

A number of embodiments of photonic crystal fibers have been described. However, further embodiments can include other types of photonic crystal fibers. For example, while the foregoing description relates to photonic crystal fibers having spiral confinement regions, the principles described herein can be applied to non-spiral photonic crystal fibers. In general, these principles can be applied to fibers composed of a confinement region with one or more concentric layers. Embodiments of photonic crystal fibers are described in the following patents, patent applications, and provisional patent applications: U.S. Pat. No. 6,625,364, entitled "LOW-LOSS PHOTONIC CRYSTAL WAVEGUIDE HAVING LARGE CORE RADIUS;" U.S. Pat. No. 6,563,981, entitled "ELECTROMAGNETIC MODE CONVERSION IN PHOTONIC CRYSTAL MULTIMODE WAVEGUIDES;" U.S. patent application Ser. No. 10/057,440, entitled "PHOTONIC CRYSTAL OPTICAL WAVEGUIDES HAVING TAILORED DISPERSION PROFILES," and filed on Jan. 25, 2002; U.S. patent application Ser. No. 10/121,452, entitled "HIGH INDEX-CONTRAST FIBER WAVEGUIDES AND APPLICATIONS," and filed on Apr. 12, 2002; U.S. Pat. No. 6,463,200, entitled "OMNIDIRECTIONAL MULTILAYER DEVICE FOR ENHANCED OPTICAL WAVEGUIDING;" Provisional 60/428,382, entitled "HIGH POWER WAVEGUIDE," and filed on Nov. 22, 2002; U.S. patent application Ser. No. 10/196,403, entitled "METHOD OF FORMING REFLECTING DIELECTRIC MIRRORS," and filed on Jul. 16, 2002; U.S. patent application Ser. No. 10/720, 606, entitled "DIELECTRIC WAVEGUIDE AND METHOD OF MAKING THE SAME," and filed on Nov. 24, 2003; U.S. patent application Ser. No. 10/733,873, entitled "FIBER WAVEGUIDES AND METHODS OF MAKING SAME," and filed on Dec. 10, 2003; Provisional Patent Application No. 60/603,067, entitled "PHOTONIC CRYSTAL WAVEGUIDES AND SYSTEMS USING SUCH WAVEGUIDES," and filed on Aug. 20, 2004. The contents of each of the above mentioned patents, patent applications, and provisional patent applications are hereby incorporated by reference in their entirety.

Moreover, while the foregoing embodiments pertain to photonic crystal fibers having solid confinement regions, photonic crystal fibers can also include confinement regions with portions that are not solid, such as holey fibers.

The photonic crystal fibers described herein may be used in a variety of applications. For example, the photonic crystal fibers can be used in medical laser systems. Referring to FIG. 5, an example of a medical laser system 500 includes a $CO_2$ laser 510, and a photonic crystal fiber 520 having a hollow core to guide radiation 512 from the laser to a target location 99 of a patient. Radiation 512 has a wavelength of 10.6 microns. Laser radiation 512 is coupled by a coupling assembly 530 into the hollow core of photonic crystal fiber 520, which delivers the radiation through a handpiece 540 to target location 599. During use, an operator (e.g., a medical practitioner, such as a surgeon, a dentist, an ophthalmologist, or a veterinarian) grips a portion 542 of handpiece 540, and manipulates the handpiece to direct laser radiation 513 emitted from an output end of photonic crystal fiber 520 to target location 599 in order to perform a therapeutic function at the target location. For example, the radiation can be used to excise, incise, ablate, or vaporize tissue at the target location.

$CO_2$ laser 510 is controlled by an electronic controller 550 for setting and displaying operating parameters of the system. The operator controls delivery of the laser radiation using a remote control 552, such as a foot pedal. In some embodiments, the remote control is a component of handpiece 540, allowing the operator to control the direction of emitted laser radiation and delivery of the laser radiation with one hand or both hands.

In addition to grip portion 542, handpiece 540 includes a stand off tip 544, which maintains a desired distance (e.g., from about 0.1 millimeters to about 30 millimeters) between the output end of fiber 520 and target tissue 599. The stand off tip assist the operator in positioning the output end of photonic crystal fiber 520 from target location 599, and can also reduce clogging of the output end due to debris at the target location. In some embodiments, handpiece 540 includes optical components (e.g., a lens or lenses), which focus the beam emitted from the fiber to a desired spot size. The waist of the focused beam can be located at or near the distal end of the stand off tip.

In some embodiments, fiber 520 can be easily installed and removed from coupling assembly 530, and from handpiece 540 (e.g., using conventional fiber optic connectors). This can facilitate ease of use of the system in single-use applications, where the fiber is replaced after each procedure.

Typically, $CO_2$ laser 510 has an average output power of about 5 Watts to about 80 Watts at 10.6 microns (e.g., about 10 Watts or more, about 20 Watts or more). In many applications, laser powers of about 5 Watts to about 30 Watts are sufficient for the system to perform its intended function. For example, where system 500 is being used to excise or incise tissue, the radiation is confined to a small spot size and a laser having an average output power in this range is sufficient.

In certain embodiments, however, laser 510 can have an output power as high as about 100 Watts or more (e.g., up to about 500 Watts). For example, in applications where system 500 is used to vaporize tissue over a relatively large area (e.g., several square millimeters or centimeters), extremely high power lasers may be desirable.

Photonic crystal fiber can deliver the radiation from laser 510 to the target location with relatively high efficiency. For example, the fiber average output power can be about 50% or more of the fiber input energy (e.g., about 60% or more, about 70% or more, about 80% or more). Accordingly, the fiber's output power can be about 3 Watts or more (e.g., about 8 Watts or more, about 10 Watts or more, about 15 Watts or more). In certain embodiments, however, the average output power from the fiber can be less than 50% of the laser power, and still be sufficiently high to perform the intended procedure. For example, in some embodiments, the fiber average output power can be from about 20% to about 50% of the laser average output power.

The length of photonic crystal fiber 520 can vary as desired. In some embodiments, the fiber is about 1.2 meters long or more (e.g., about 1.5 meters or more, about 2 meters or more, about 3 meters or more, about 5 meters or more). The length is typically dependent on the specific application for which the laser system is used. In applications where laser 510 can be positioned close to the patient, and/or where the range of motion of the handpiece desired for the application is relatively small, the length of the fiber can be relatively short (e.g., about 1.5 meters or less, about 1.2 meters or less, about 1 meter or less). In certain applications, the length of fiber 520 can be very short (e.g., about 50 centimeters or less, about 20 centimeters or less, about 10 centimeters or less). For example, very short lengths of photonic crystal fiber may be useful in procedures where the system can deliver radiation from the laser to the fiber by some other means (e.g., a different waveguide or an articulated arm). Very short fiber lengths may be useful for nose and ear procedures, for example.

However, in applications where it is inconvenient for the laser to be placed in close proximity to the patient and/or where a large range of motion of the handpiece is desired, the length of the fiber is longer (e.g., about 2 meters or more, about 5 meters or more, about 8 meters or more). For example, in surgical applications, where a large team of medical practitioners is needed in close proximity to the patient, it may be desirable to place the laser away from the operating table (e.g., in the corner of the operating room, or in a different room entirely). In such situations, a longer fiber may be desirable.

In general, photonic crystal fiber 520 is flexible, has a bend plane, and can be bent to relatively small radii of curvature over relatively large angles without significantly impacting its performance (e.g., without causing the fiber to fail, or without reducing the fiber transmission to a level where the system cannot be used for its intended use while the fiber is bent). In some embodiments, an operator can bend photonic crystal fiber 520 to have a relatively small radius of curvature, such as about 15 cm or less (e.g., about 10 cm or less, about 8 cm or less, about 5 cm or less, about 3 cm or less) while still delivering sufficient power to the target location for the system to perform its function.

In general, the angle through which the fiber is bent can vary, and usually depends on the procedure being performed. For example, in some embodiments, the fiber can be bent through about 90° or more (e.g., about 120° or more, about 150° or more).

Losses of transmitted power due to the operator bending photonic crystal fiber 520 may be relatively small. In general, losses due to bends should not significantly damage the fiber, e.g., causing it to fail, or reduce the fiber output power to a level where the system can no longer perform the function for which it is designed. Embodiments of photonic crystal fiber 520 (e.g., about 1 meter or more in length) can be bent through 90° with a bend radius of about 5 centimeters or less, and still transmit about 30% or more (e.g., about 50% or more, about 70% or more) of radiation coupled into the fiber at the guided wavelength. These fibers can provide such transmission characteristics and provide average output power of about 3 Watts or more (e.g., about 5 Watts or more, about 8 Watts or more, about 10 Watts or more).

The quality of the beam of the laser radiation emitted from the output end of fiber 520 can be relatively good. For example, the beam can have a low $M^2$ value, such as about 4 or less (e.g., about 3 or less, about 2.5 or less, about 2 or less). $M^2$ is a parameter commonly used to describe laser beam quality, where an $M^2$ value of about 1 corresponds to a $TEM_{00}$ beam emitted from a laser, which has a perfect Gaussian profile. The $M^2$ value is related to the minimum spot size that can be formed from the beam according to the formula:

$$d_s = 1.27 f \lambda M^2 / d_b$$

where $d_s$ is the minimum spot diameter, $d_b$ is the beam diameter prior to being focused to the spot by a lens having focal length f. Accordingly, the minimum possible spot size a beam can be focused is proportional to the $M^2$ value for the beam. Practically, beams having smaller values of $M^2$ can provide higher radiation power densities to the target area, with less damage to surrounding tissue due to the decreased spot size.

The spot size of radiation delivered by photonic crystal fiber 520 to the target tissue can be relatively small. For example, in certain embodiments, the spot can have a diameter of about 500 microns or less (e.g., about 300 microns or less, about 200 microns or less, such as about 100 microns) at a desired working distance from the fiber's output end (e.g., from about 0.1 mm to about 3 mm). As discussed previously, a small spot size is desirable where system 500 is being used to excise or incise tissue or in other applications where substantial precision in the delivery of the radiation is desired. Alternatively, in applications where tissue is to be ablated or vaporized, and/or a lesser level of precision is sufficient, the spot size can be relatively large (e.g., having a diameter of about 2 millimeters or more, about 3 millimeters or more, about 4 millimeters or more).

While laser 510 is a $CO_2$ laser, photonic crystal fibers can be used in medical laser systems that use other types or lasers, operating at wavelengths different from 10.6 microns. In general, medical laser systems can provide radiation at ultraviolet (UV), visible, or infrared (IR) wavelengths. Lasers delivering IR radiation, for example, emit radiation having a wavelength between about 0.7 microns and about 20 microns (e.g., between about 2 to about 5 microns or between about 8 to about 12 microns). Waveguides having hollow cores, such as photonic crystal fiber 520, are well-suited for use with laser systems having wavelengths of about 2 microns or more, since gases that commonly occupy the core have relatively low absorptions at these wavelengths compared to many dielectric materials (e.g., silica-based glasses and various polymers). In addition to $CO_2$ lasers, other examples of lasers which can emit IR radiation include Nd:YAG lasers (e.g., at 1.064 microns), Er:YAG lasers (e.g., at 2.94 microns), Er, Cr: YSGG (Erbium, Chromium doped Yttrium Scandium Gallium Garnet) lasers (e.g., at 2.796 microns), Ho:YAG lasers (e.g., at 2.1 microns), free electron lasers (e.g., in the 6 to 7 micron range), and quantum cascade lasers (e.g., in the 3 to 5 micron range).

In general, the type of laser used in a medical laser system depends on the purpose for which the system is designed. The type of laser can be selected depending on whether the system is to be used in surgical procedures, in diagnosis, or in physiologic studies. For example, an argon laser, which delivers in the blue and green regions of the visible light spectrum, with two energy peaks, at 488 nm and 514 nm, can be used for photocoagulation. A dye laser, which is a laser with organic dye dissolved in a solvent as the active medium whose beam is in the visible light spectrum, can be used in photodynamic therapy. Excimer lasers provide radiation in the ultraviolet spectrum, penetrates tissues only a small distance, can be used to break chemical bonds of molecules in tissue instead of generating heat to destroy tissue. Such lasers can be used in opthalmological procedures and laser angioplasty. Ho:YAG lasers can provide radiation in the near infrared spectrum and can be used for photocoagulation and photoablation. Krypton lasers provide radiation in the yellow-red visible light spectrum, and can be used for photocoagulation. Radiation from KTP lasers can be frequency-doubled to provide radiation in the green visible light spectrum and can be used for photoablation and photocoagulation. Nd:YAG lasers can be for photocoagulation and photoablation. Pulsed dye lasers can be used to provide in the yellow visible light spectrum (e.g., with a wavelength of 577 nm or 585 nm), with alternating on and off phases of a few microseconds each, and can be used to decolorize pigmented lesions.

In general, laser systems can use continuous wave or pulsed lasers. Furthermore, while $CO_2$ lasers are typically used at average output powers of about 5 Watts to about 100 Watts, photonic crystal fibers can generally be used with a variety of laser powers. For example, average laser power can be in the milliWatt range in certain systems, up to as much as several hundred Watts (e.g., about 200 Watts or more) in extremely high power systems.

In general, for high power systems, the average power density guided by fiber 520 can be extremely high. For example, power density in the fiber, or exiting the fiber's core) can be about $10^3$ $W/cm_2$ or more (e.g., about $10^4$ $W/cm^2$ or more, about $10^5$ $W/cm^2$ or more, $10^6$ $W/cm^2$ or more).

Figure 6A:
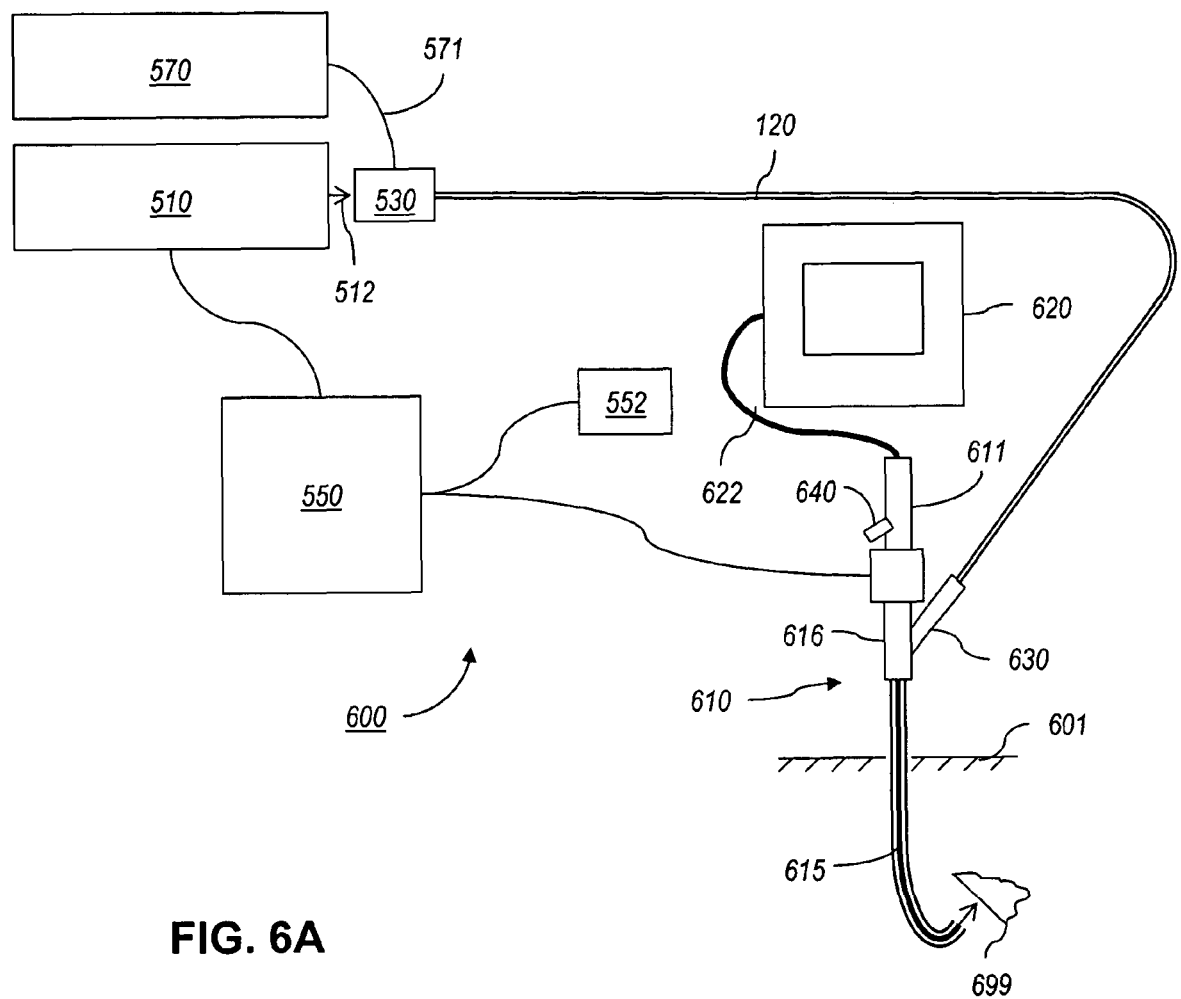
FIG. 6A is a schematic diagram of a medical laser system that includes a photonic crystal fiber and an endoscope.

In certain embodiments, handpieces can include actuators that allow the operator to bend the fiber remotely, e.g., during operation of the system. For example, referring to FIG. 6A, in some embodiments, laser radiation 512 can be delivered to target tissue 699 within a patient 601 using an endoscope 610. Endoscope 610 includes a gripping portion 611 and a flexible conduit 615 connected to each other by an endoscope body 616. An imaging cable 622 housing a bundle of optical fibers is threaded through a channel in gripping portion 611 and flexible conduit 615. Imaging cable 622 provide illumination to target tissue 699 via flexible conduit 615. The imaging cable also guides light reflected from the target tissue to a controller 620, where it is imaged and displayed providing visual information to the operator. Alternatively, or additionally, the endoscope can include an eyepiece lens that allows the operator to view the target area directly through the imaging cable.

Endoscope 610 also includes an actuator 640 that allows the operator to bend or straighten flexible conduit 615. In some embodiments, actuator 640 allows flexible conduit 615 to bend in one plane only, e.g., in the bend plane of fiber 520. Alternatively, in certain embodiments, the actuator allow the flexible conduit to bend in more than one plane.

Endoscope 610 further includes an auxiliary conduit 630 (e.g., a detachable conduit) that includes a channel through which fiber 520 is threaded. The channel connects to a second channel in flexible conduit 615, allowing fiber 520 to be threaded through the auxiliary conduit into flexible conduit 615. Fiber 520 is attached to auxiliary conduit in a matter than maintains the orientation of the fiber with respect the channel through flexible conduit 615, thereby minimizing twisting of the photonic crystal fiber about its waveguide axis within the flexible conduit. In embodiments where photonic crystal fiber 520 has a confinement region that includes a seam, the fiber can be attached to the auxiliary conduit so that the seam is not coincident with a bend plane of the flexible conduit.

In general, photonic crystal fibers can be used in conjunction with commercially-available endoscopes, such as endoscopes available from PENTAX Medical Company (Montvale, N.J.) and Olympus Surgical & Industrial America, Inc. (Orangeburg, N.Y.).

Figure 6B:
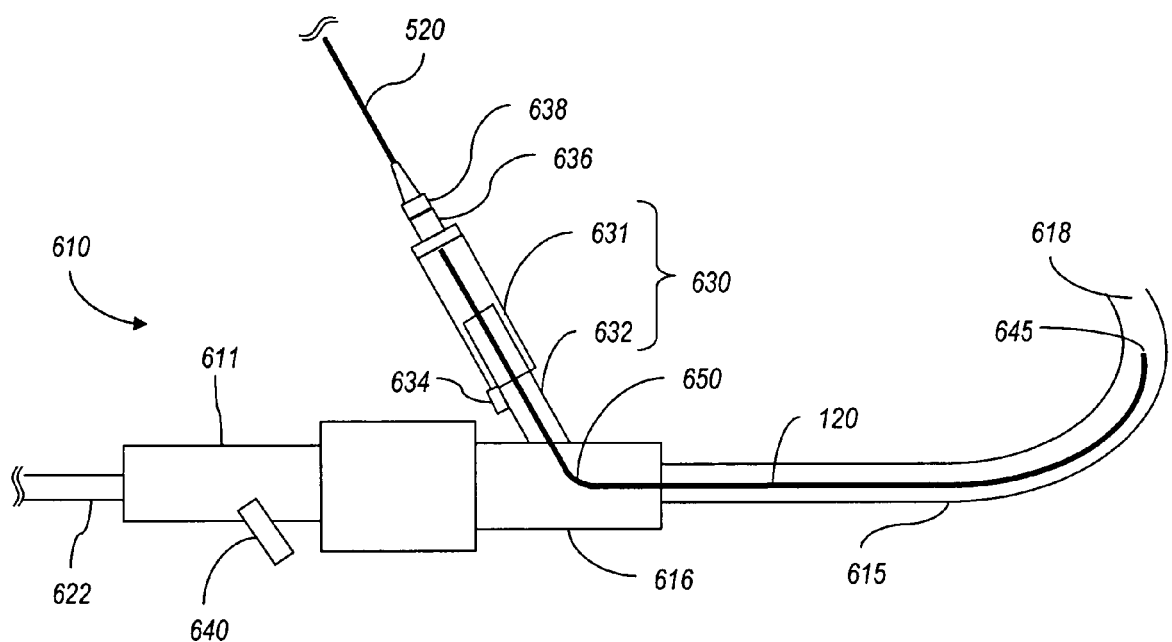
FIG. 6B is a schematic diagram of the endoscope shown in FIG. 6A.

Auxiliary conduit 630 can be configured to allow the user to extend and/or retract the output end of the photonic crystal fiber within flexible conduit 615. For example, referring to FIG. 6B, in some embodiments, auxiliary conduit 630 of endoscope 610 can include two portions 631 and 632 that are moveable with respect to each other. Portion 632 is attached to endoscope body 616, while portion 631 telescopes with respect to portion 632. Portion 632 includes a connector 636 that connects to a fiber connector 638 attached to fiber 520. The mating mechanism of connector 636 and fiber connector 638 can allow for quick and simple removal and attachment of the photonic crystal fiber to the endoscope. When attached, connector 636 and fiber connector 638 substantially prevent fiber 520 from twisting, maintaining its orientation about the fiber axis within flexible conduit 615. The connectors can maintain the orientation of the fiber in the conduit with a seam in the fiber oriented away from a bend plane of the conduit, for example. Furthermore, when portion 631 extends or retracts with respect to portion 632, it extends or retracts the output end 645 of fiber 520 with respect to the distal end 618 of flexible conduit 615. Auxiliary conduit 630 also includes a locking mechanism 634 (e.g., a latch or clamp) that allows the user to lock the portion 631 with respect to portion 632. The locking mechanism prevents unwanted movement of fiber 520 within flexible conduit 615 while radiation is being delivered to the patient. The channel in body 616 through which fiber 520 is threaded includes a kink 650. Connector 638 can be configured so that a seam in the fiber has a particular orientation with respect to kink 650. For example, the seam can be positioned so that it is not on the outside of the bend that the fiber experiences at kink 650. In some embodiments, the connectors can orient the seam on the inside of the bend at kink 650.

In general, laser systems that utilize photonic crystal fibers can be used in a number of different medical procedures. For example, laser systems can be used in aesthetic medical procedures, surgical medical procedures, ophthalmic procedures, veterinary procedures, and/or dental procedures.

Aesthetic procedures include treatment for: hair removal; pulsed light skin treatments for reducing fine wrinkle lines, sun damage, age spots, freckles, some birthmarks, rosacea, irregular pigmentation, broken capillaries, benign brown pigment and pigmentation; skin resurfacing; leg veins; vascular lesions; pigmented lesions; acne; psoriasis & vitiligo; and/or cosmetic repigmentation.

Surgical procedures include procedures for gynecology, laparoscopy, condylomas and lesions of the external genitalia, and/or leukoplakia. Surgical applications can also include ear/nose/throat (ENT) procedures, such as laser assisted uvula palatoplasty (LAUP) (i.e., to stop snoring); procedures to remove nasal obstruction; stapedotomy; tracheobronchial endoscopy; tonsil ablation; and/or removal of benign laryngeal lesions. Surgical applications can also include breast biopsy, cytoreduction for metastatic disease, treatment of decubitus or statis ulcers, hemorrhoidectomy, laparoscopic surgery, mastectomy, and/or reduction mammoplasty. Surgical procedures can also include procedures in the field of podiatry, such as treatment of neuromas, periungual, subungual and plantar warts, porokeratoma ablation, and/or radical nail excision. Other fields of surgery in which lasers may be used include orthopedics, urology, gastroenterology, and thoracic & pulmonary surgery.

Ophthalmic uses include treatment of glaucoma, age-related macular degeneration (AMD), proliferative diabetic retinopathy, retinopathy of prematurity, retinal tear and detachment, retinal vein occlusion, and/or refractive surgery treatment to reduce or eliminate refractive errors.

Veterinary uses include both small animal and large animal procedures.

Examples of dental applications include hard tissue, soft tissue, and endodontic procedures. Hard tissue dental procedures include caries removal & cavity preparation and laser etching. Soft tissue dental procedures include incision, excision & vaporization, treatment of gummy smile, coagulation (hemostasis), exposure of unerupted teeth, aphthous ulcers, gingivoplasty, gingivectomy, gingival troughing for crown impressions, implant exposure, frenectomy, flap surgery, fibroma removal, operculectomy, incision & drainage of abscesses, oral papilectomy, reduction of gingival hypertrophy, pre-prosthetic surgery, pericoronitis, peri implantitis, oral lesions, and sulcular debridement. Endodontic procedures include pulpotomy, root canal debridement, and cleaning. Dental procedures also include tooth whitening.

Generally, the type of laser, wavelength, fiber length, fiber outer diameter, and fiber inner diameter, among other system parameters, are selected according to the application. For example, embodiments in which laser 510 is a $CO_2$ laser, laser systems 500 or 600 can be used for surgical procedures requiring the ablation, vaporization, excision, incision, and coagulation of soft tissue. $CO_2$ laser systems can be used for surgical applications in a variety of medical specialties including aesthetic specialties (e.g., dermatology and/or plastic surgery), podiatry, otolaryngology (e.g., ENT), gynecology (including laparoscopy), neurosurgery, orthopedics (e.g., soft tissue orthopedics), arthroscopy (e.g., knee arthroscopy), general and thoracic surgery (including open surgery and endoscopic surgery), dental and oral surgery, ophthalmology, genitourinary surgery, and veterinary surgery.

In some embodiments, $CO_2$ laser systems can be used in the ablation, vaporization, excision, incision, and/or coagulation of tissue (e.g., soft tissue) in dermatology and/or plastic surgery in the performance of laser skin resurfacing, laser derm-abrasion, and/or laser burn debridement. Laser skin resurfacing (e.g., by ablation and/or vaporization) can be performed, for example, in the treatment of wrinkles, rhytids, and/or furrows (including fine lines and texture irregularities). Laser skin resurfacing can be performed for the reduction, removal, and/or treatment of: keratoses (including actinic keratosis), seborrhoecae vulgares, seborrheic wart, and/or verruca seborrheica; vermillionectomy of the lip; cutaneous horns; solar/actinic elastosis; cheilitis (including actinic cheilitis); lentigines (including lentigo maligna or Hutchinson's malignant freckle); uneven pigmentation/dyschromia; acne scars; surgical scars; keloids (including acne keloidalis nuchae); hemangiomas (including Buccal, port wine and/or pyogenic granulomas/granuloma pyogenicum/ granuloma telagiectaticum); tattoos; telangiectasia; removal of skin tumors (including periungual and/or subungual fibromas); superficial pigmented lesions; adenosebaceous hypertrophy and/or sebaceous hyperplasia; rhinophyma reduction; cutaneous papilloma; milia; debridement of eczematous and/ or infected skin; basal and squamous cel carcinoma (including keratoacanthomas, Bowen's disease, and/or Bowenoid Papulosis lesions); nevi (including spider, epidermal, and/or protruding); neurofibromas; laser de-epithelialization; tricoepitheliomas; xanthelasma palpebrarum; and/or syringoma. $CO_2$ laser systems can be used for laser ablation, vaporization and/or excision for complete and/or partial nail matrixectomy, for vaporization and/or coagulation of skin lesions (e.g., benign and/or malignant, vascular and/or avascular), and/or for Moh's surgery, for lipectomy. Further examples include using laser system 1300 for laser incision and/or excision of soft tissue for the performance of upper and/or lower eyelid blepharoplasty, and/or for the creation of recipient sites for hair transplantation.

In certain embodiments, $CO_2$ laser systems is used in the laser ablation, vaporization, and/or excision of soft tissue during podiatry procedures for the reduction, removal, and/or treatment of: verrucae vulgares/plantar warts (including paronychial, periungual, and subungual warts); porokeratoma ablation; ingrown nail treatment; neuromas/fibromas (including Morton's neuroma); debridement of ulcers; and/or other soft tissue lesions. $CO_2$ laser systems can also be used for the laser ablation, vaporization, and/or excision in podiatry for complete and/or partial matrixectomy.

$CO_2$ laser systems can be used for laser incision, excision, ablation, and/or vaporization of soft tissue in otolaryngology for treatment of: choanal atresia; leukoplakia (including oral, larynx, uvula, palatal, upper lateral pharyngeal tissue); nasal obstruction; adult and/or juvenile papillomatosis polyps; polypectomy of nose and/or nasal passages; lymphangioma removal; removal of vocal cord/fold nodules, polyps and cysts; removal of recurrent papillomas in the oral cavity, nasal cavity, larynx, pharynx and trachea (including the uvula, palatal, upper lateral pharyngeal tissue, tongue and vocal cords); laser/tumor surgery in the larynx, pharynx, nasal, ear and oral structures and tissue; Zenker' diverticulum/pharynoesophageal diverticulum (e.g., endoscopic laser-assisted esophagodiverticulostomy); stenosis (including subglottic stenosis); tonsillectomy (including tonsillar cryptolysis, neoplasma) and tonsil ablation/tonsillotomy; pulmonary bronchial and tracheal lesion removal; benign and malignant nodules, tumors and fibromas (e.g., of the larynx, pharynx, trachea, tracheobronchial/endobronchial); benign and/or malignant lesions and/or fibromas (e.g., of the nose or nasal passages); benign and/or malignant tumors and/or fibromas (e.g., oral); stapedotomy/stapedectomy; acoustic neuroma in the ear; superficial lesions of the ear (including chondrodermatitis nodularis chronica helices/Winkler's disease); telangiectasia/hemangioma of larynx, pharynx, and/or trachea (including uvula, palatal, and/or upper lateral pharyngeal tissue); cordectomy, cordotomy (e.g., for the treatment of vocal cord paralysis/vocal fold motion impairment), and/or cordal lesions of larynx, pharynx, and/or trachea; myringotomy/tympanostomy (e.g., tympanic membrane fenestration); uvulopalatoplasty (e.g., LAUP); turbinectomy and/or turbinate reduction/ablation; septal spur ablation/reduction and/or septoplasty; partial glossectomy; tumor resection on oral, subfacial and/or neck tissues; rhinophyma; verrucae vulgares; and/or gingivoplasty/gingivectomy.

In some embodiments, $CO_2$ laser systems can be used for the laser incision, excision, ablation, and/or vaporization of soft tissue in gynecology for treatment of: conizaton of the cervix (including cervical intraepithelial neoplasia, vulvar and/or vaginal intraepithelial neoplasia); condyloma acuminata (including cervical, genital, vulvar, preineal, and/or Bowen's disease, and/or Bowenoid papulosa lesions); leukoplakia (e.g., vulvar dystrophies); incision and drainage of Bartholin's and/or nubuthian cysts; herpes vaporization; urethral caruncle vaporization; cervical dysplasia; benign and/or malignant tumors; and/or hemangiomas.

$CO_2$ laser systems can be used for the vaporization, incision, excision, ablation and/or coagulation of soft tissue in endoscopic and/or laparoscopic surgery, including gynecology laparoscopy, for treatment of: endometrial lesions (including ablation of endometriosis); excision/lysis of adhesions; salpingostomy; oophorectomy/ovariectomy; fimbroplasty; metroplasty; tubal microsurgery; uterine myomas and/or fibroids; ovarian fibromas and/or follicle cysts; uterosacral ligament ablation; and/or hysterectomy.

In certain embodiments, $CO_2$ laser systems are used for the laser incision, excision, ablation, and/or vaporization of soft tissue in neurosurgery for the treatment of cranial conditions, including: posterior fossa tumors; peripheral neurectomy; benign and/or malignant tumors and/or cysts (e.g., gliomos, menigiomas, acoustic neuromas, lipomas, and/or large tumors); arteriovenous malformation; and/or pituitary gland tumors. In some embodiments, $CO_2$ laser systems are used for the laser incision, excision, ablation, and/or vaporization of soft tissue in neurosurgery for the treatment of spinal cord conditions, including: incision/excision and/or vaporization of benign and/or malignant tumors and/or cysts; intra- and/or extradural lesions; and/or laminectomy/laminotomy/microdisectomy.

$CO_2$ laser systems can be used for the incision, excision, and/or vaporization of soft tissue in orthopedic surgery in applications that include arthroscopic and/or general surgery. Arthroscopic applications include: menisectomy; chondromalacia; chondroplasty; ligament release (e.g., lateral ligament release); excision of plica; and/or partial synovectomy. General surgery applications include: debridement of traumatic wounds; debridement of decubitis and/or diabetic ulcers; microsurgery; artificial joint revision; and/or polymer (e.g., polymethylmethacrylate) removal.

$CO_2$ laser systems can also be used for incision, excision, and/or vaporization of soft tissue in general and/or thoracic surgery, including endoscopic and/or open procedures. Such applications include: debridement of decubitus ulcers, stasis, diabetic and other ulcers; mastectomy; debridement of burns; rectal and/or anal hemorrhoidectomy; breast biopsy; reduction mammoplasty; cytoreduction for metastatic disease; laparotomy and/or laparoscopic applications; mediastinal and/or thoracic lesions and/or abnormalities; skin tag vaporization; atheroma; cysts (including sebaceous cysts, pilar cysts, and/or mucous cysts of the lips); pilonidal cyst removal and/or repair; abscesses; and/or other soft tissue applications.

In certain embodiments, $CO_2$ laser systems can be used for the incision, excision, and/or vaporization of soft tissue in dentistry and/or oral surgery, including for: gingivectomy; gingivoplasty; incisional and/or excisional biopsy; treatment of ulcerous lesions (including aphthous ulcers); incision of infection when used with antibiotic therapy; frenectomy; excision and/or ablation of benign and/or malignant lesions; homeostasis; operculectomy; crown lengthening; removal of soft tissue, cysts, and/or tumors; oral cavity tumors and/or hemangiomas; abscesses; extraction site hemostasis; salivary gland pathologies; preprosthetic gum preparation; leukoplakia; partial glossectomy; and/or periodontal gum resection.

In some embodiments, $CO_2$ laser systems can be used for incision, excision, and/or vaporization of soft tissue in genitourinary procedures, including for: benign and/or malignant lesions of external genitalia; condyloma; phimosis; and/or erythroplasia.

Figure 7:
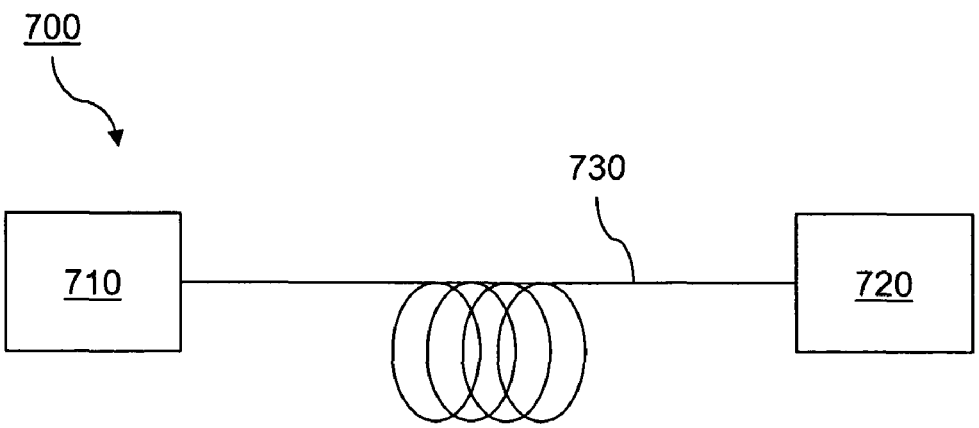
FIG. 7 is a schematic diagram of an optical telecommunication system that implements photonic crystal fibers described herein.

In addition to medical applications, photonic crystal fibers such as those described herein can be used in other applications as well. In some embodiments, photonic crystal fibers can be used to guide radiation between a source and a detector. FIG. 7 shows a schematic diagram of a system 700 including a source 710 and a detector 720, which are coupled to one another by a photonic crystal fiber 730. In certain embodiments, system 700 is an optical telecommunication system and photonic crystal fiber 730 serves as an optical transmission line to guide optical signals between source 710 and detection system 720. In general, the optical transmission line may include one or more other segments in addition to photonic crystal fiber 730. Source 710 may be the original source of an optical signal directed along the transmission line or it may be an intermediate node that redirects the optical signal to the transmission line, optically amplifies it, and/or electronically detects it and optically regenerates it. Furthermore, source 710 may include components for multiplexing or demultiplexing multiple optical signals at different wavelengths. Similarly, detector 720 may be the final destination for the optical signal transmitted along the transmission line, or it may be an intermediate node that redirects, optically amplifies, and/or electrically detects and optically regenerates the optical signal. In addition, detector 720 may also include components for multiplexing or demultiplexing multiple optical signals at different wavelengths. The optical signal transmitted along the transmission line may be a WDM signal that includes multiple signals at corresponding wavelengths. Suitable wavelengths for the system include those within a range of about 1.2 microns to about 1.7 microns, which corresponds to many long-haul systems in use today, as well those within a range of about 0.7 microns to about 0.9 microns, which corresponds to some metro systems currently being considered.

Because of their small losses, the photonic crystal fibers described herein may provide one or more advantages when used as the transmission fiber in an optical telecommunications system. Because the losses are small, the lengths of the transmission line can be made larger as periodic amplification is less necessary. For example, the losses may be smaller than 1 dB/km, smaller than 0.1 dB/km, or even smaller than 0.01 dB/km. Moreover, because FWM is reduced, WDM channel spacing in the fiber can be made smaller.

In some embodiments, system 700 may be a diagnostic tool. For example, photonic crystal fiber 730 can be used as a sample cell in a gas-phase spectrometer, where the hollow core of fiber 730 is filled with a sample gas. Radiation launched into fiber 730 interacts with the gas. Typically, the amount of radiation at different wavelengths depends on the composition of the gas in the core. Thus, by monitoring the intensity of radiation exiting the fiber at different wavelengths, one can determine the composition of the gas. In such embodiments, detector 720 can be connected to a processor (e.g., a computer), which performs an analysis of a signal generated by detector 720 in response to radiation from the source. An example of a gas phase spectrometer utilizing a hollow fiber is described by C. Charlton et al., in *IEEE Proc.-Optoelectron.*, Vol. 150, No. 4, pp. 306-309.

Figure 8:
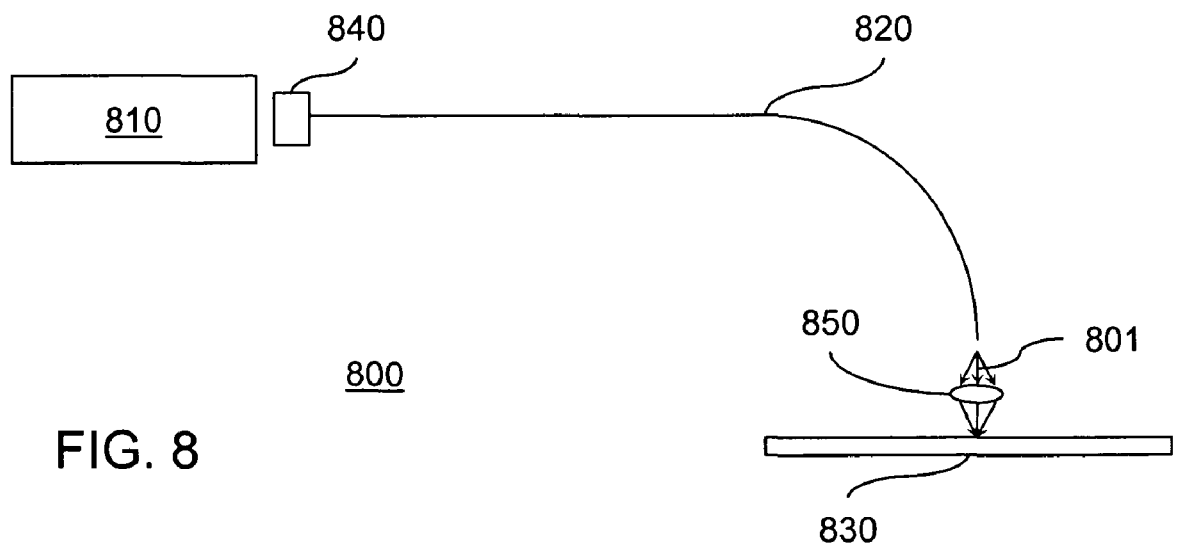
FIG. 8 is a schematic diagram of a laser system that implements photonic crystal fibers described herein.

In some embodiments, a photonic crystal fiber, such as those described above, can be used to deliver laser radiation to a target. For example, referring to FIG. 8, a laser system 800 includes a laser 810 and a photonic crystal fiber 820 for guiding electromagnetic (EM) energy from the laser to a target 830 (e.g., a sheet of steel or a patient) remote from the laser. Radiation is coupled from laser 810 into fiber 820 using a coupler 840. Laser system 800 also includes a focusing element 850 (e.g., a lens or combination of lenses) that focuses radiation 801 emerging from photonic crystal fiber 820 onto target 830. The radiation can, for example, be used to cut, clean, ablate, coagulate, form, liquefy, engrave and/or weld material at target 830. For example, in forming applications, laser radiation can be directed to a metal sheet in order to thermal stress a portion of the sheet, which causes the sheet to bend.

Laser 810 can be a continuous wave or pulsed laser. The distance between laser 810 and target 830 can vary depending on the specific application, and can be on the order of several meters or more (e.g., about 10 m or more, about 20 m or more, about 50 m or more, about 100 m or more).

Laser system 800 can operate at UV, visible, or infrared (IR) wavelengths. In some embodiments, photonic crystal fiber 820 is configured to guide IR energy emitted by laser 810, and the energy has a wavelength between about 0.7 microns and 20 microns (e.g., between about 2 to 5 microns or between about 8 to 12 microns). In some embodiments, laser 1210 is a $CO_2$ laser and the radiation has a wavelength of about 6.5 microns or 10.6 microns. Other examples of lasers which can emit IR energy include Nd:YAG lasers (e.g., at 1.064 microns) Er:YAG lasers (e.g., at 2.94 microns), Er, Cr:YSGG (Erbium, Chromium doped Yttrium Scandium Gallium Garnet) lasers (e.g., at 2.796 microns), Ho:YAG lasers (e.g., at 2.1 microns), free electron lasers (e.g., in the 6 to 7 micron range), and quantum cascade lasers (e.g., in the 3 to 5 micron range).

The power emitted from laser 810 at the guided wavelength can vary. Although the laser power can be relatively low, e.g., mW, in many applications the laser system is operated at high powers. For example, the laser output intensity can be about one Watt or more (e.g., about five Watts or more, about 10 Watts or more, about 20 Watts or more). In some applications, the laser output energy can be about 100 Watts or more (e.g., about 200 Watts or more, about 300 Watts or more, about 500 Watts or more, about 1 kilowatt or more).

For high power systems, the power density guided by fiber 820 can be relatively high. For example, power density in the fiber can be about $10^5$ $W/cm^2$ or more, such as about $10^6$ $W/cm^2$ or more, about $10^7$ $W/cm^2$ or more, about $10^8$ $W/cm^2$ or more, about $10^9$ $W/cm^2$ or more, about $10^{10}$ $W/cm^2$ or more.

Fiber 1820 can have relatively low losses at the guided wavelength (e.g., about 10 dB/m or less, about 5 dB/m or less, about 2 dB/m or less, about 1 dB/m or less, about 0.5 dB/m or less, about 0.2 dB/m or less). Due to the low loss, only a relatively small amount of the guided energy is absorbed by the fiber, allowing the fiber to guide high power radiation without substantial damage due to heating.

Coupler 840 can be any coupler suitable for the wavelength and intensity at which the laser system operates. One type of a coupler is described by R. Nubling and J. Harrington in "Hollow-waveguide delivery systems for high-power, industrial $CO_2$ lasers," *Applied Optics*, 34, No. 3, pp. 372-380 (1996). Other examples of couplers include one or more focusing elements, such as one or more lenses. Coupling efficiency can be high. For example, coupler 140 can couple about 70% or more of the laser output into a guided mode in the fiber (e.g., about 80% or more, about 90% or more, about 95% or more, about 98% or more). Coupling efficiency refers to the ratio of power guided away by the desired mode to the total power incident on the fiber.

Other embodiments are within the scope of the following claims.

What is claimed is:
1. A photonic crystal fiber comprising:
   a core extending along a waveguide axis;
   a confinement region extending along the waveguide axis, the confinement region surrounding the core; and
   a cladding extending along the waveguide axis, the cladding surrounding the confinement region, wherein the cladding has an asymmetric cross-section that extends along a length of the photonic crystal fiber, the cladding having a short cross-sectional dimension, a, and a long cross-sectional dimension, b, and an ellipticity, ∈, given by the formula:

$$\varepsilon = \frac{(b-a)}{\frac{1}{2}(b+a)},$$

that is in a range from about 0.05 to about 0.5.

2. The photonic crystal fiber of claim 1 wherein the confinement region comprises a layer of a first material arranged in a spiral structure that extends along the waveguide axis and the asymmetric cross-section causes the photonic crystal fiber to bend preferably in a plane that does not intersect an end of the spiral structure that is adjacent the core.

3. The photonic crystal fiber of claim 1 wherein the photonic crystal fiber is configured to guide radiation at a wavelength λ along the waveguide axis and the confinement region comprises a peridoic structure that substantially confines the radiation to the core.

4. The photonic crystal fiber of claim 3 wherein the cladding comprises a layer of a first material surrounding the confinement region, the layer having a thickness along a direction normal to the waveguide axis that is larger than the period of the periodic structure of the confinement region.

5. The photonic crystal fiber of claim 1 wherein the asymmetric cross-section causes the photonic crystal fiber to bend preferably in a bend plane relative to other planes.

6. The photonic crystal fiber of claim 1 wherein the confinement region comprises a seam extending along the waveguide axis.

7. The photonic crystal fiber of claim 6 wherein the confinement region comprises a layer of a first material that is arranged in a spiral around the waveguide axis and the seam is the end of the layer that is adjacent the core.

8. The photonic crystal fiber of claim 6 wherein the short cross-sectional dimension, a, is non-coincident with the seam.

9. The photonic crystal fiber of claim 8 wherein the seam is located in a range from about 80 degrees to about 110 degrees from the short cross-sectional dimension.

10. The photonic crystal fiber of claim 1 wherein the confinement region comprises a layer of a first dielectric material arranged in a spiral around the waveguide axis.

11. The photonic crystal fiber of claim 10 wherein the confinement region further comprises a layer of a second dielectric material arranged in a spiral around the waveguide axis, the second dielectric material having a different refractive index from the first dielectric material.

12. The photonic crystal fiber of claim 11 wherein the first dielectric material is a glass.

13. The photonic crystal fiber of claim 12 wherein the glass is a chalcogenide glass.

14. The photonic crystal fiber of claim 13 wherein the second dielectric material is a polymer.

15. The photonic crystal fiber of claim 1 wherein the confinement region comprises at least one layer of a chalcogenide glass.

16. The photonic crystal fiber of claim 1 wherein the confinement region comprises at least one layer of a polymeric material.

17. The photonic crystal fiber of claim 1 wherein the core is a hollow core.

18. The photonic crystal fiber of claim 1 wherein the photonic crystal fiber is configured to guide radiation at about 10.6 μm along the waveguide axis.

19. A system, comprising:
a $CO_2$ laser; and
the photonic crystal fiber of claim 1, the photonic crystal fiber having an input end that is positioned relative to the $CO_2$ laser to receive radiation from the $CO_2$ laser and the photonic crystal fiber being arranged to deliver the radiation to a target.

20. A system, comprising:
the photonic crystal fiber of claim 1, the photonic crystal fiber having an input end and an output end; and
a handpiece attached to the photonic crystal fiber,
wherein the handpiece allows an operator to control the orientation of the output end to direct the radiation to a target location of a patient.

21. The system of claim 20 wherein the handpiece comprises an endoscope.

22. The system of claim 21 wherein the endoscope comprises a flexible conduit and a portion of the photonic crystal fiber is threaded through a channel in the flexible conduit.

23. The system of claim 22 wherein the endoscope comprises an actuator mechanically coupled to the flexible conduit configured to bend a portion of the flexible conduit in at least one plane thereby allowing the operator to vary the orientation of the output end.

24. The system of claim 23 wherein the photonic crystal fiber is attached to the endoscope so that the at least one plane corresponds to the bend plane of the photonic crystal fiber.

25. The photonic crystal fiber of claim 1 wherein
the confinement region comprises a layer of a first material arranged in a spiral structure that extends along the waveguide axis and the asymmetric cross-section causes the photonic crystal fiber to bend preferably in a plane that does not intersect an end of the spiral structure that is adjacent the core.

\* \* \* \* \*

UNITED STATES PATENT AND TRADEMARK OFFICE
CERTIFICATE OF CORRECTION

PATENT NO. : 8,280,212 B2  
APPLICATION NO. : 11/366345  
DATED : October 2, 2012  
INVENTOR(S) : James Goell et al.

Page 1 of 1

It is certified that error appears in the above-identified patent and that said Letters Patent is hereby corrected as shown below:

In the claims, claim 1, column 33, line 5:

Please amend claim 1 as follows:

The line reads "ity, $\in$, given by the formula:"; please rewrite as -- ity, $\varepsilon$, given by the formula: --.

Signed and Sealed this
Fourth Day of December, 2012

David J. Kappos  
*Director of the United States Patent and Trademark Office*